United States Patent
Huang

(10) Patent No.: US 6,979,573 B2
(45) Date of Patent: *Dec. 27, 2005

(54) COMPOSITIONS AND METHODS FOR CAPTURING, ISOLATING, DETECTING, ANALYZING AND QUANTIFYING MACROMOLECULES

(75) Inventor: Chin-Shiou Huang, San Mateo, CA (US)

(73) Assignee: Aspira Biosystems, Inc., Burlingame, CA (US)

( * ) Notice: Subject to any disclaimer, the term of this patent is extended or adjusted under 35 U.S.C. 154(b) by 246 days.

This patent is subject to a terminal disclaimer.

(21) Appl. No.: 09/895,644

(22) Filed: Jun. 28, 2001

(65) Prior Publication Data

US 2002/0045275 A1 Apr. 18, 2002

Related U.S. Application Data

(62) Division of application No. 09/507,300, filed on Feb. 18, 2000, now Pat. No. 6,458,599.

(51) Int. Cl.$^7$ ............................................. G01N 33/543
(52) U.S. Cl. .............................. 436/518; 435/4; 435/6; 436/524; 436/531; 436/535
(58) Field of Search ................................ 436/518, 524, 436/531, 535; 435/4, 6; 427/2.13

(56) References Cited

U.S. PATENT DOCUMENTS

| | | | |
|---|---|---|---|
| 4,962,154 A | | 10/1990 | Pollock et al. |
| 5,110,833 A | | 5/1992 | Mosbach |
| 5,310,648 A | * | 5/1994 | Arnold et al. .................. 435/5 |
| 5,587,273 A | * | 12/1996 | Yan et al. .................... 430/269 |
| 6,057,377 A | | 5/2000 | Sasaki et al. |
| 6,217,901 B1 | | 4/2001 | Perrott et al. |
| 6,310,110 B1 | | 10/2001 | Markowitz et al. |
| 6,379,599 B1 | | 4/2002 | Viadya et al. |
| 6,458,599 B1 | | 10/2002 | Huang |

FOREIGN PATENT DOCUMENTS

| | | |
|---|---|---|
| WO | WO 01/09035 A1 | 2/2001 |
| WO | WO 01/61354 A1 | 8/2001 |

OTHER PUBLICATIONS

Rachkov, A. et al. "Towards Molecularly Imprinted Polymers Selective To Peptides And Proteins. The Epitope Approach." *Biochimica et biophysica Acta*, 1544: 255–266, 2001.

Rachkov, A. et al. "Recognition of Oxytocin and Oxytocin–Related Peptides In Aqueous Media Using A Molecularly Imprinted Polymer Synthesized By The Epitope Approach." *J. Chromatogr. A*, 889: 111–118, 2000.

Glad, et al., 1985, "Use of Silane Monomers for Molecular Imprinting and Enzyme Entrapment in Polysiloxane–Coated Porous Silica," *J. Chrom.* 347: 11–23.

Leonhardt, et al., 1987, "Enzyme–Mimicking Polymers Exhibiting Specific Substrate Binding and Catalytic Functions," *Reactive Polymers* 6: 285–290.

Markowitz et al, 1999, "Catalytic Silica Particles via Template–Directed Molecular Imprinting" *Langmuir* 2000: 1759–1765.

Sellergren, et al., 1985, "Molecular Imprinting of Amino Acid Derivatives in Macroporous Polymers," *J. Chrom.* 347: 1–10.

Karmalkar et al., 1996, Molecularly Imprinted Hydrogels Exhibit Chymotrypsin–like Activity, *Macromolecules*, 29(4): 1366–1368.

Peppas et al., 1999,Poly(ethylene glycol)–containing hydrogels in drug delivery *Journal of Controlled Release* 62: 81–87.

* cited by examiner

*Primary Examiner*—Christopher L. Chin

(57) ABSTRACT

The present invention provides imprint compositions useful for capturing, isolating, detecting and/or quantifying macromolecules in a sample, methods of making and using the same. Generally, the imprint compositions comprise a matrix material defining an imprint of a template molecule, and the template molecule typically corresponds to a portion of a macromolecule of interest.

32 Claims, 7 Drawing Sheets

SEQUENCE LISTING

```
<160> NUMBER OF SEQ ID NOS: 2

<210> SEQ ID NO 1
<211> LENGTH: 7
<212> TYPE: PRT
<213> ORGANISM: Equus sp.

<400> SEQUENCE: 1

Leu Lys Lys Ala Thr Asn Glu
1               5

<210> SEQ ID NO 2
<211> LENGTH: 7
<212> TYPE: PRT
<213> ORGANISM: rabbit

<400> SEQUENCE: 2

Thr Lys Val Ile Ser Glu Glu
1               5
```

COMPOSITIONS AND METHODS FOR CAPTURING, ISOLATING, DETECTING, ANALYZING AND QUANTIFYING MACROMOLECULES

This application is a divisional of U.S. patent application Ser. No. 09/507,300, filed Feb. 18, 2000, now U.S. Pat. No. 6,458,599, which is herein incorporated by reference.

1. FIELD OF THE INVENTION

The present invention is directed to molecular imprints able to selectively bind macromolecules. The molecular imprints of the present invention can be prepared without obtaining a purified sample of a target macromolecule. A template molecule possessing the structure of a portion of the macromolecule is synthesized and then imprinted. Molecular imprints made by this method form selective complexes with their target macromolecules. Arrays of molecular imprints can be used to rapidly and inexpensively screen diverse biological samples.

2. BACKGROUND OF THE INVENTION

The recent explosion in the number of novel macromolecules, many identified by the genome sequencing efforts, has intensified the need for improved compositions and methods for separating macromolecules. Thousands of recently identified macromolecules have yet to be purified and characterized functionally. Techniques for the rapid capture, isolation, detection, analysis, and quantification of macromolecules would accelerate the functional characterization of novel macromolecules.

In particular, when the macromolecule is a protein, current methods of capture and separation are cumbersome and expensive. In one current technique, affinity matrices are used to capture and/or separate a protein of interest from a mixture of proteins and other molecules. Affinity matrices might be prepared using a purified sample of the protein to create antibodies. However, the preparation of antibodies that specifically bind a protein can take several months and might even require a purified sample of the protein. Alternatively, an affinity matrix might be prepared using knowledge of the function of the macromolecule. For instance, an affinity matrix based on a binding partner of the protein might be used for capture and separation of the protein. Unfortunately, methods of separating macromolecules that require extensive knowledge about the macromolecule, or even a purified sample of the macromolecule, are ineffective with macromolecules that have yet to be characterized. The requirement of a purified sample of the macromolecule for the preparation or selection of an affinity matrix often presents researchers with nothing more than frustrating circularity.

In addition to affinity matrices, other techniques are also used to separate macromolecules. For example, the current state of the art technique for separating large numbers of proteins is two-dimensional gel electrophoresis. The technique typically resolves about 2,000 proteins, and the best gels can resolve up to 11,000 proteins (Abbot, 1999, Nature 402:715–720). Unfortunately, many researchers require separation techniques that can resolve proteins from samples as diverse as the entire protein fraction of a mammalian cell. The protein fraction of a cell can contain tens of thousands of proteins, overwhelming the resolving power of 2D electrophoresis (Abbot, 1999, supra). Since the full sequences of the genomes of many species, including humans, are nearing completion, researchers must now grapple with the functions of hundreds of thousands of novel macromolecules (Abbot, 1999, supra). New techniques of macromolecular separation that require limited information or even no information about the target macromolecules are needed.

Currently, researchers are seeking improvements in protein separation. For instance, some are attempting to create chips which specifically bind proteins. In one typical chip, antibodies specific for known proteins are attached to a substrate to form a microarray. These chips can then be used to bind and identify proteins from a complex solution (Abbot, 1999, supra). However, these chips suffer from the same limitations of antibody production that plague affinity matrices. For each protein to be bound by the chip, a unique antibody must be prepared by an expensive process that can take several months. In addition, many proteins are not sufficiently immunogenic to create antibodies for binding.

In the field of small molecules, the technique of molecular imprinting has provided an efficient method for the preparation of matrices that are capable of selectively binding a target molecule. To prepare a molecular imprint, a matrix is formed around a template molecule. After the matrix has formed and the template molecule is removed, the matrix can then be used to selectively bind the template molecule. As early as 1949, a silica gel was created that selectively bound a dye (Dickey, 1949, Proc. Natl. Acad. Sci. USA 35:227–229). Recently, an imprint prepared with phenyl-α-D-mannopyranoside was sufficiently selective to resolve a racemic mixture of the saccharide (Wulff, 1998, supra).

Current methods form imprints of molecules in organic polymers (Wulff, 1998, Chemtech 28:19–26). To create cavities of defined shape, polymerizable molecules are bound, covalently or noncovalently, to a template molecule (Wulff, 1998, supra). The resulting complex is copolymerized in the presence of a large amount of a cross-linking reagent (Wulff, 1998, supra). The templates are then removed leaving microcavities with defined shapes and arrangements of functional groups (Wulff, 1998, supra). Imprints made by such a technique display selective binding for the template molecule. Molecular imprints have been used for chromatographic separation, immunoassays, chemosensors, and even catalysis (Wulff, 1998, supra).

To date, molecular imprints have had limited application to the binding of larger molecules including macromolecules. In fact, one review states that only small molecules can be imprinted with any great confidence. Molecular imprints of larger molecules like nucleic acids, peptides, proteins and cells fail because larger molecules yield more heterogeneous binding sites and because larger molecules can be too fragile for conventional methods of molecular imprinting (Cormack and Mosbach, 1999, Reactive and Functional Polymers 41:115–124).

Nevertheless, a few successful imprints of larger molecules have been produced. Synthetic polymers which selectively bind amino acid derivatives and peptides were created using the target amino acid derivative or peptide as a template (Kemp, 1996, Anal. Chem. 68:1948–1953). Imprints have also been created which bind to nucleotide derivatives (Spivak and Shea, 1998, Macromolecules 31:2160–2165). Ionic molecular images of polypeptides have been created by mixing a matrix-material with the intact polypeptide chain to be bound by the molecular image (U.S. Pat. No. 5,756,717). Molecular imprints of cytochrome c, hemoglobin and myoglobin, respectively, have been prepared by polymerizing acrylamide in the presence of each intact protein (U.S. Pat. No. 5,814,223). An imprint of horse myoglobin selectively bound horse myoglobin from a mixture of proteins including whale myoglobin (U.S. Pat. No. 5,814,223).

Although current methods of molecular imprinting have shown limited initial success at selectively binding macromolecules, the current methods are not sufficient for the efficient capture of macromolecules. The current techniques for molecular imprinting require a purified sample of the macromolecule to be bound by the imprint. The inability to produce a specific imprint in the absence of a purified sample of the macromolecule is no different from one of the failings of conventional methods of protein separation. In addition, current methods of preparing molecular imprinting are not amenable to creating the thousands of imprints often required by current large-scale experiments. Purification of hundreds or thousands of proteins to create a matrix for separating the proteins of a cell extract is no more efficient that 2D electrophoresis. An efficient method for producing compositions that selectively bind macromolecules given limited information about the structure or function of those macromolecules is needed. An ideal method could produce a composition capable of binding a macromolecule given as little information as a partial primary structure of the macromolecule.

An improvement in molecular imprinting to enable the preparation of affinity matrices in the absence of a purified sample of the macromolecule would overcome many limitations of the art of molecular imprinting. Techniques are also needed to efficiently separate and identify thousands of proteins. Compositions with specificity for macromolecules that can be produced rapidly and at low cost will enable such techniques. Ideal compositions would be arrays of such binding compositions, each composition designed to bind a given macromolecule. Such an array could be used to rapidly screen a complex biological sample for a number of different macromolecules simultaneously.

3. SUMMARY OF THE INVENTION

These and other shortcomings in the art are overcome by the instant invention, which in one aspect provides imprint compositions useful for capturing, isolating, detecting and/or quantifying macromolecules in a sample. Generally, the imprint compositions comprise a matrix material defining an imprint of a template molecule. The template molecule typically corresponds to a portion of a macromolecule of interest, such as, for example, a polynucleotide, a polypeptide, polysaccharide, a protein, a glycoprotein, a receptor, an enzyme, a nucleic acid, a carbohydrate, etc. If the macromolecule is composed of n identifiable structural units as defined below, then the template molecule can correspond to a portion of the macromolecule that includes from 1 up to (n−1) of those structural units. Alternatively, the template molecule can correspond to as little as 1% of the macromolecule or to as much as 99% of the macromolecule. The portion to which the template molecule corresponds may be an internal portion of the macromolecule or a terminal portion of the macromolecule. Alternatively, the portion may be a side-group or modification of the macromolecule, such as a polysaccharide group of a glycoprotein macromolecule, or a portion thereof. Preferably, the template molecule will correspond to a contiguous terminal portion of the macromolecule.

Matrix materials that can comprise the imprint compositions of the invention include substances that are capable of undergoing a physical change from a fluid state to a semi-solid or solid state. In the fluid state, the particles of a matrix material move easily among themselves, and the material retains little or no definite form. A matrix material in the fluid state can be mixed with other compounds, including template molecules. In the semi-solid or solid state, the matrix materials are capable of forming and retaining cavities that complement the shape of template molecules. Examples of such matrix materials include heat sensitive hydrogels such as agarose, polymers such as acrylamide, and cross-linked polymers.

The imprint compositions of the invention may take a variety of different forms. For example, they may be in the form of individual beads, disks, ellipses, or other regular or irregular shapes (collectively referred to as "beads"), or in the form of sheets. Each bead or sheet may comprise imprint cavities of a single template molecule, or they may comprise imprint cavities of two or more different template molecules. In one embodiment, the imprint composition comprises imprint cavities of a plurality of different template molecules arranged in an array or other pattern such that the relative positions of the imprint cavities within the array or pattern correlate with their identities, i.e. the identities of the template molecules used to create them. Each position or address within the array may comprise an imprint cavity of a single template molecule, or imprint cavities of a plurality of different template molecules, depending upon the application. Moreover, the entire array or pattern may comprise unique imprint cavities, or may include redundancies, depending upon the application.

As discussed above, the template molecule used to make the imprint will typically correspond to a portion of a macromolecule of interest. However, as will be discussed more thoroughly below, an important aspect of the invention includes the ability to use the imprint compositions of the invention to isolate novel macromolecules from complex mixtures and/or samples. In this embodiment, a template molecule can have a structure that does not necessarily correspond to a portion of any known macromolecule. Rather, the template molecule could have a structure that corresponds to a portion of a consensus sequence derived from a family of macromolecules. Alternatively, the template molecule might have a random structure. A molecular imprint of a template molecule can bind a novel macromolecule if the template molecule corresponds to a portion of the novel macromolecule. An array of imprints of template molecules can be used to rapidly screen a mixture for novel macromolecules. An array of imprints of the complete set of polymeric template molecules composed of a defined number of monomers can be used to capture most or all of the macromolecules of a mixture.

In another aspect, the present invention provides methods of making the imprint compositions of the invention. According to the method, a compound or mixture of compounds that is capable of undergoing a change of physical state such that the resultant product is a solid or semi-solid matrix capable of retaining shaped cavities is contacted with a template molecule under conditions in which the change of physical state is effected. Changing the physical state of the compound or mixture of compounds in the presence of the template molecule results in a solid or semisolid matrix having the template molecules entrapped therein. The template molecules are then removed, yielding a solid or semisolid matrix defining cavities that correspond in shape to the template molecules. This resultant product is a molecular imprint composition. Particularly preferred methods of making molecular imprint compositions include the method of surface imprinting described in copending application Ser. No. 09/507,299, filed concurrently herewith, which is incorporated herein by reference.

In still another aspect, the present invention provides methods of using the imprint compositions to capture, isolate, detect, analyze and/or quantify a macromolecule of interest in a sample. According to the method, a sample suspected of containing a macromolecule of interest is contacted with an imprint composition of the invention under conditions in which the macromolecule binds the imprint composition. The imprint-macromolecule complex may be optionally rinsed to remove unbound components of the sample. The macromolecule may be dissociated from the complex and isolated and/or quantified. Alternatively, the presence of the macromolecule may be detected, and/or its quantity determined, without dissociating it from the complex.

The methods can be used to capture macromolecules of known, partially known or unknown structure. In the former two embodiments, the imprint composition comprises an imprint of a template molecule that corresponds to a known portion of the macromolecule of interest. In the latter embodiment, the imprint may comprise an imprint of a template molecule that corresponds to a conserved portion of a specific class of macromolecules, such as for example, a conserved portion of a receptor superfamily or family, or it may comprise a predicted sequence or a completely random sequence. These latter imprint compositions can be used to capture and/or isolate novel members of known classes of macromolecules, or completely new types of macromolecules.

Macromolecules may be detected, captured, isolated, analyzed and/or quantified according to the methods of the invention singly, using an imprint composition specific for a particular macromolecule of interest, or alternatively, pluralities of different macromolecules can be captured simultaneously from a complex mixture using, for example, the array or pattern imprint compositions described herein, for subsequent detection, isolation and/or quantification.

The methods and compositions of the invention provide significant advantages over currently available protein separations and molecular imprinting technologies. Unlike known imprinting techniques, the molecular imprints of the present invention do not require a purified sample of a target macromolecule for preparation. The primary structure of a portion of the macromolecule is sufficient to create an imprint that can specifically capture the macromolecule. If the target macromolecule is novel, a molecular imprint of template molecules that do not necessarily correspond to portions of known macromolecules can be used to screen for the target macromolecule. Because they do not require isolation of the macromolecule of interest, the molecular imprints of the present invention can be prepared in far less time and at a fraction of the cost of conventional protein separation media.

The methods and compositions of the invention also have widespread applicability, ranging from the detection and/or isolation of specific macromolecules of interest from samples, to the capture, isolation, analysis and/or quantification of pluralities of macromolecules from complex mixtures for applications such as, for example, expression profiling, to the discovery of novel members of known classes of macromolecules and/or completely new types of molecules altogether.

4. BRIEF DESCRIPTION OF THE FIGURES

Figure 5:
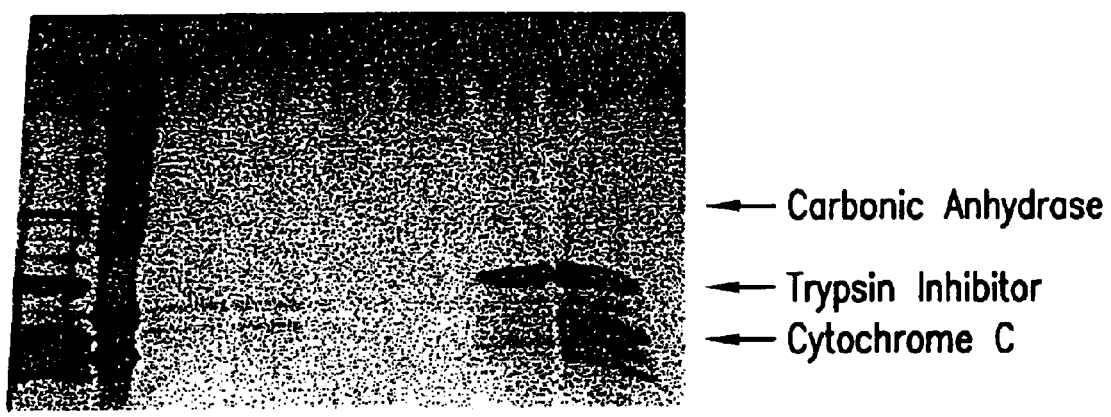
Figure 6:
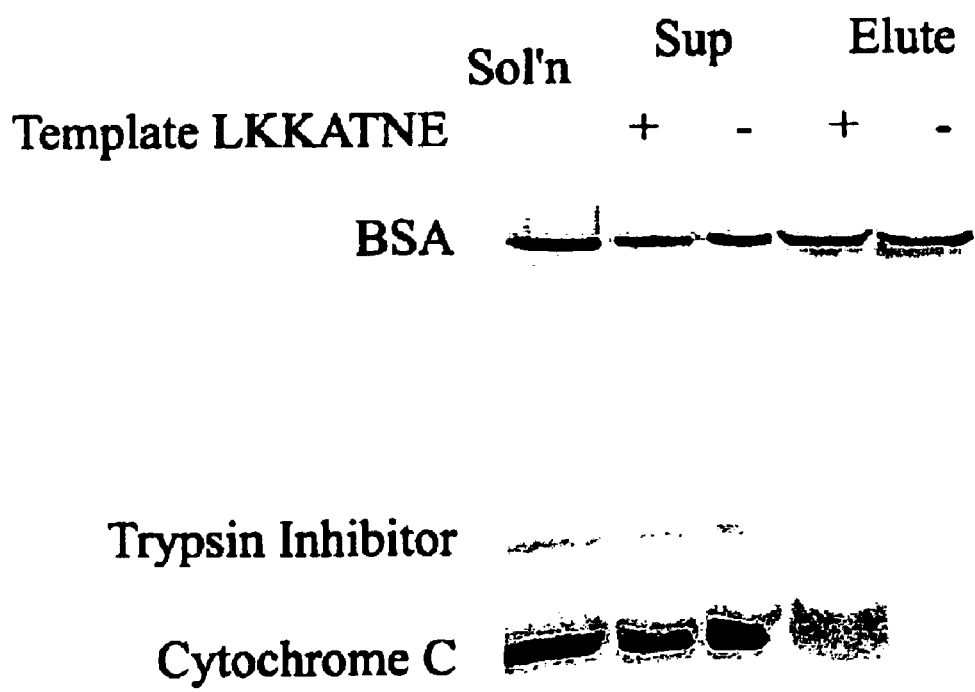
Figure 7:
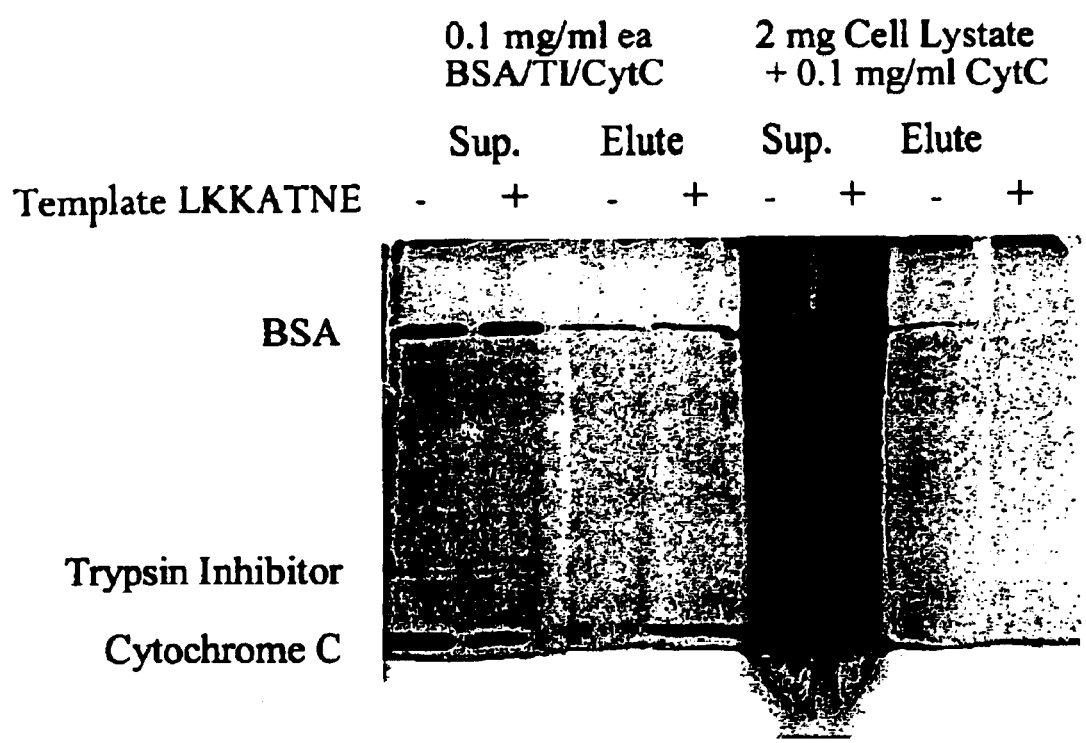

FIG. 5 provides an SDS-PAGE analysis of a capture experiment performed with a molecular imprint according to the present invention;

FIG. 6 provides an SDS-PAGE analysis of a capture and isolation experiment performed with a surface imprint of the present invention; and FIG. 7 provides an SDS-PAGE analysis of experiments capturing and isolating cytochrome c from a mixture and from a cell lysate with surface imprints of the present invention.

5. DETAILED DESCRIPTION OF THE INVENTION

Current methods of macromolecular separation are inefficient when applied to novel macromolecules. Small molecules have been successfully captured and separated with molecular imprints for many years (Wulff, 1998, supra). However, molecular imprinting has limited application to the separation of macromolecules. Only a few imprints of macromolecules have been described, and those imprints required purified samples of the macromolecule for preparation. There is a need for improvement in the field of macromolecular separation, and the field of molecular imprinting requires improvement to be useful for the separation of macromolecules.

The present invention provides compositions and methods that overcome the limitations of macromolecule separation and molecular imprinting. The invention is based, in part, on the Applicant's discovery that a molecular imprint made with a template molecule that corresponds in structure to a portion of a macromolecule of interest can be used to specifically capture and/or isolate that macromolecule from a sample. Until Applicant's discovery, conventional techniques required a purified sample of the macromolecule to prepare a molecular imprint with specificity for the macromolecule.

The present invention overcomes the limitations that prevented broad application of molecular imprinting to the capture of macromolecules. The use of molecular imprints is no longer limited to the subset of macromolecules for which a purified sample is available. Molecular imprinting can now be applied to capture macromolecules using only a limited amount of information about the macromolecule. If the primary structure of as little as a portion of the macromolecule is available, then one can use the techniques of the present invention to rapidly create an inexpensive affinity medium with specificity for the macromolecule. For instance, when one has obtained the primary structure of a portion of a protein from the sequence of a nucleic acid encoding the protein, one has enough information to create a molecular imprint to specifically capture the protein.

5.1 Abbreviations

As used herein, the abbreviations for the genetically encoded L-enantiomeric amino acids are conventional and are as follows:

| Amino Acid | One-Letter Symbol | Common Abbreviation |
|---|---|---|
| Alanine | A | Ala |
| Arginine | R | Arg |
| Asparagine | N | Asn |
| Aspartic acid | D | Asp |
| Cysteine | C | Cys |
| Glutamine | Q | Gln |
| Glutamic acid | E | Glu |
| Glycine | G | Gly |
| Histidine | H | His |
| Isoleucine | I | Ile |
| Leucine | L | Leu |
| Lysine | K | Lys |
| Methionine | M | Met |
| Phenylalanine | F | Phe |
| Proline | P | Pro |
| Serine | S | Ser |
| Threonine | T | Thr |
| Tryptophan | W | Trp |
| Tyrosine | Y | Tyr |
| Valine | V | Val |

The abbreviations used for the D-enantiomers of the genetically encoded amino acids are lower-case equivalents of the one-letter symbols. For example, "R" designates L-arginine and "r" designates D-arginine. When a polypeptide sequence is represented as a series of three-letter or one-letter amino acid abbreviations, it will be understood that the left-hand direction is the amino terminal direction and the right-hand direction is the carboxy terminal direction, in accordance with standard usage and convention.

5.2 The Invention

In one aspect, the invention provides imprint compositions comprising a matrix material having a cavity of a template molecule imprinted therein/thereon. The template molecule typically corresponds to a portion of a macromolecule of interest, but may also have a structure that corresponds to a consensus sequence from a family of macromolecules or a random structure. The imprint composition can be used to detect the presence of the macromolecule in a sample, to capture, isolate, detect, analyze and/or quantify the macromolecule from a sample.

5.2.1 Macromolecules

Macromolecules that can be captured, isolated, detected, analyzed and/or quantified using the imprint compositions of the invention include any type of macromolecule from which a template molecule can be designed and constructed according to the principles taught herein. Virtually any type of macromolecule can be captured, isolated, detected, analyzed and/or quantified using the methods and compositions of the invention. Non-limiting examples include biological polymers such as polypeptides, polynucleotides and polysaccharides, non-biological polymers such as polyesters, polyethers, polyurethanes, block co-polymers, and other polymers known to those of skill in the art and biological and non-biological non-polymeric compounds such as antibiotics, steroids, natural products, dyes, etc. Thus, non-limiting examples of the myriad types of macromolecules that may be captured, isolated, detected, analyzed and/or quantified using the methods and compositions of the invention include cytokines, hormones, growth factors, enzymes, cofactors, ligands, receptors, antibodies, carbohydrates, steroids, therapeutics, antibiotics, and even larger structures such as viruses or cells, and other macromolecular targets that will be apparent to those of skill in the art.

It will be understood that as used herein, the expression "macromolecule" is not intended to place specific size limitations upon the molecules that may be captured with the imprint compositions of the present invention. Rather, "macromolecules" as used herein refers to molecules that comprise a plurality of structural moieties such that a template molecule corresponding to at least one of the structural moieties can be used to prepare a molecular imprint capable of binding the macromolecule. Template molecules and the formation of a molecular imprints are discussed in more detail below.

The identities of the structural moieties that comprise macromolecules as used herein will depend upon the nature of the macromolecule, and may include regions of primary, secondary and/or tertiary structure of the macromolecule. For example, for polypeptide macromolecules the structural moieties may be the individual amino acids composing the polypeptide, or alternatively, if the polypeptide has several structural domains, as is often the case with, e.g., enzymes and antibodies, the structural moieties may be the individual structural domains. For example, an antibody macromolecule may be viewed as being composed of individual amino acids, or Fab and Fc structural domains, or alternately, Fab' and Fc structural domains, etc., depending upon the proteolytic enzymes used to digest the antibody. A glycosylated polypeptide may be viewed as being composed of individual amino acids or structural domains as described above and/or saccharide or oligosaccharide structural moieties. A polynucleotide macromolecule may be viewed as being composed of individual nucleotide structural moieties.

Structural moieties may also be regions of secondary structure, such as regions of α-helix, β-sheet, β-barrel, etc. of proteins or regions of A-form helix, B-form helix, Z-form helix, triple helix, etc. of polynucleotides.

For non-polymeric macromolecules such as, for example, antibiotics, the structural moieties may be the various core groups composing the antibiotic. For example, polyene antibiotics such as amphotericin B and nystatin may be viewed as being composed of polyene macrocycle and saccharide structural moieties.

As will be discussed in more detail below, the macromolecule will preferably comprise a combination of one or more structural moieties that, when taken together, uniquely identify the macromolecule over closely related macromolecules. Template molecules derived from such macromolecules can be used to make imprint compositions according to the invention that are capable of selectively capturing or binding the macromolecule from a complex mixture and/or sample.

Due to their ability to be uniquely defined by their primary structure (i e., primary sequence of monomers), polymers are preferred template molecules according to the invention. The most preferred polymers are biological polymers such as polypeptides, polynucleotides and polysaccharides.

Polypeptides include polymers of two or more amino acids known to those of skill in the art, and derivatives known to those of skill in the art such as glycopeptides. Polynucleotides include polymers of two or more nucleotides and can be DNA or RNA of natural or synthetic origin. Polynucleotides can be single-stranded, double-stranded, or multiply stranded. Polysaccharides include polymers of two or more sugars and can be linear or branched. The monomer subunits of biological polymers can be those that occur naturally, or synthetic analogs of such monomers known to those of skill in the art.

The macromolecules according to the invention may be derived from virtually any source. They may be obtained from natural sources such as biological samples or from synthetic sources. In particular, the imprint compositions of the present invention can be used to capture and isolate macromolecules from biological sources as complex as a cell or tissue lysate. The imprint compositions can also be used to purify a synthetic macromolecule from a mixture of precursors and byproducts. The imprint compositions can even be used to resolve a racemic mixture of synthetic macromolecules.

5.2.2 Template Molecules

The imprint compositions of the invention are prepared from a template molecule. In many embodiments, the template molecule has a structure that corresponds to a portion of the macromolecule of interest. A template molecule "corresponds" to a portion of the macromolecule if it possesses the structural features of that portion of the macromolecule and substantially no other structural features of the macromolecule outside that portion. The template molecule can possess structural features of the macromolecule by way of structural identity with the portion of the macromolecule. Alternatively, the template molecule can possess structural features of the portion of the macromolecule by approximating or mimicking the structure of at least one structural moiety of the portion of the macromolecule.

Figure 1A:
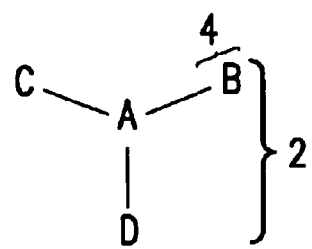
FIG. 1A illustrates a macromolecular target that can be captured with an imprint composition of the present invention.
Figure 1B:
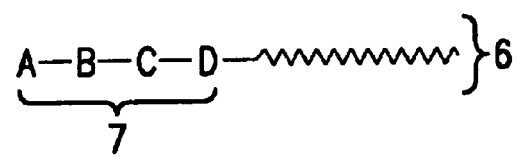
FIG. 1B illustrates a polymeric macromolecular target.
Figure 1C:
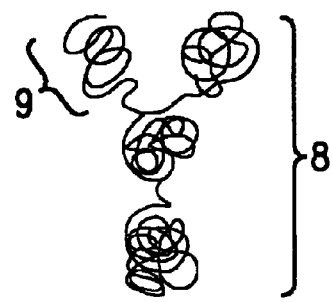
FIG. 1C illustrates a polymeric macromolecular target with a superstructure.

Template molecules that correspond to portions of known macromolecules can be prepared according to known principles. In general, for any given macromolecule, a portion of the structure of the macromolecule is used to prepare or select a template molecule that corresponds in structure to that portion of the macromolecule. For example, referring to FIG. 1A, a molecular imprint composition with specificity for macromolecule 2 can be prepared with a template molecule that corresponds to structural unit 4 of the macromolecule. For a polymeric macromolecule 6, as illustrated in FIG. 1B, a template molecule can correspond to contiguous sequence of monomers 7. Polymeric macromolecule 8, illustrated in FIG. 1C, has a macromolecular superstructure, and the template molecule can correspond to domain 9 of the macromolecule.

Figure 2:
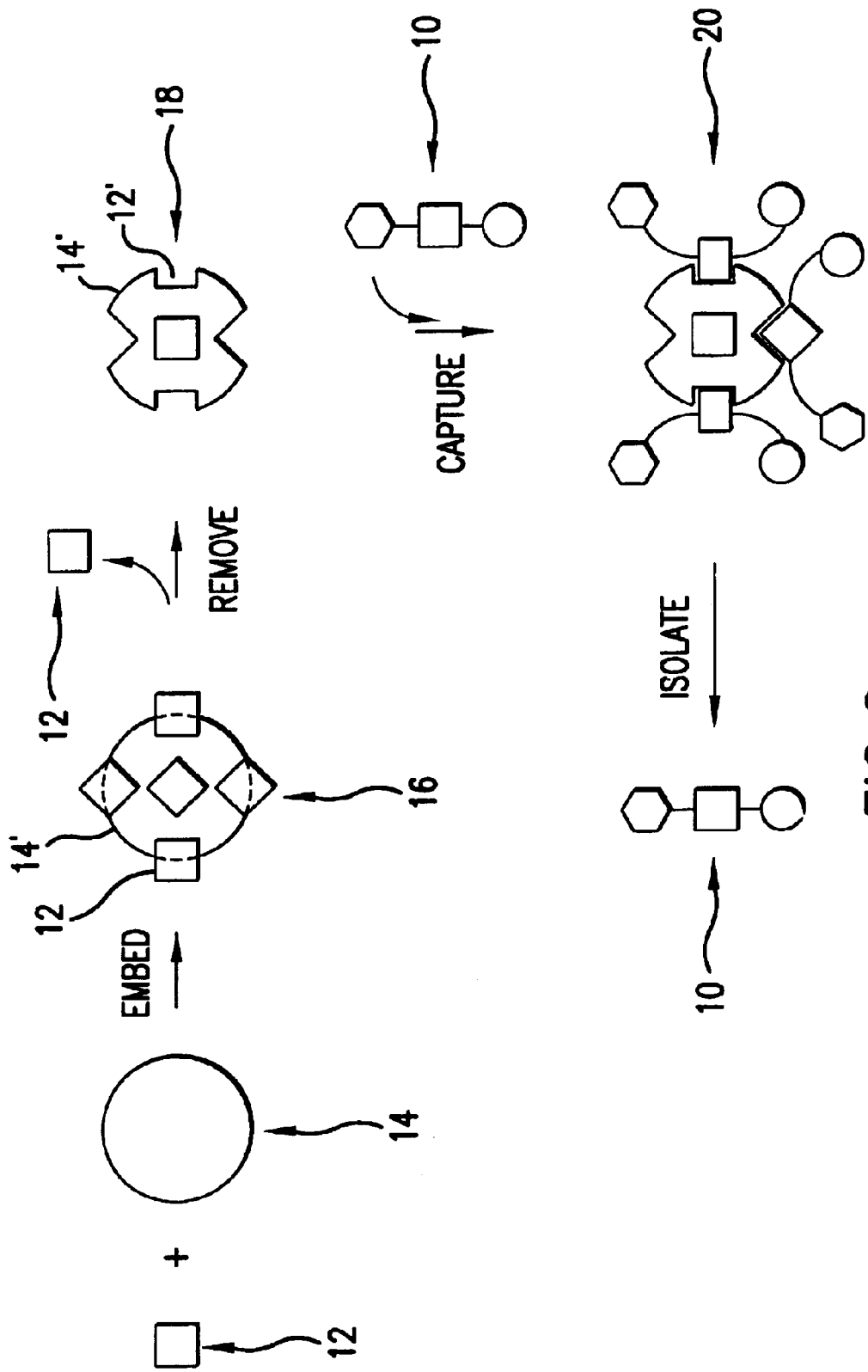
FIG. 2 illustrates the preparation of a molecular imprint of a template molecule that corresponds in structure to a portion of a macromolecule and subsequent capture and isolation of the macromolecule.

The correspondence between the topography of the template molecule and the topography of the portion of the macromolecule should be close enough so that the portion of the macromolecule fits specifically within an imprint or a cavity formed by the template molecule (see, e.g., FIG. 2). In general, for any macromolecule that comprises a plurality of structural groups, the template molecule can correspond to at least one of the structural groups of the macromolecule. For example, if the macromolecule is an antibiotic such as erythromycin, a template molecule can correspond to one of the sugar moieties of erythromycin. If the macromolecule is a polymer, a preferred template molecule would consist of a series of monomer units that is identical to a contiguous series of monomer units of a portion of the polymer.

For example, referring to FIG. 1B, when the macromolecule is a polypeptide, the template molecule may be a peptide having an amino acid sequence that identically corresponds to the amino acid sequence of a contiguous region of the polypeptide macromolecule. If the polypeptide macromolecule is glycosylated, the template molecule may be an oligosaccharide having a primary sequence of saccharides that corresponds identically to the primary saccharide sequence of all or a portion of the glycosyl groups. If the macromolecule is a polynucleotide, the template molecule may be an oligonucleotide having a nucleotide sequence that corresponds identically to the nucleotide sequence of a contiguous region of the polynucleotide macromolecule. When the polynucleotide is single-stranded, the template molecule will be single-stranded. When the polynucleotide is double-stranded, the template molecule can be either single-stranded or double-stranded, depending upon whether the resultant imprint composition will be used to capture, isolate detect, analyze and/or quantify the polynucleotide under native or denaturing conditions. If single-stranded, the template molecule may correspond to either strand of the double-stranded polynucleotide macromolecule.

Those of skill in the art will recognize that a template molecule need not have exact structural identity with the portion of the macromolecule in order to correspond to that portion. Often, a template molecule may incorporate topographic substitutions. A substitution is "topographic" if the topography of the template molecule creates a cavity that binds or captures the corresponding portion of the macromolecule. Preferably, a template including a topographic substitution creates an imprint that specifically binds the corresponding portion of the target macromolecule. Template molecules comprising topographic substitutions, and that therefore do not correspond identically to a portion of the macromolecule, are said to correspond substantially to the macromolecule. Thus, unless specifically indicated otherwise, as used herein, the expression "corresponds to" is intended to encompass those situations where a template molecule corresponds identically or substantially to a macromolecule of interest.

When constructing a template molecule that does corresponds substantially to a portion of the macromolecule, the template molecule should be topographically of a size that is similar to or larger than the portion of the macromolecule, so that the macromolecule can fit within or bind the imprint cavity created by the template molecule. For example, since Phe and Tyr have side chains of similar structure, and the Phe side chain can be viewed as a "sub-set" of the Tyr side chain, a template molecule having a Phe or Tyr corresponds to a macromolecule Phe. Similarly, a template molecule Cys, Ser or Thr corresponds to a macromolecule Ser. Thus, Tyr is a topographic substitution of Phe, and Ser and Thr are topographic substitutions of Cys. For the twenty genetically encoded amino acids, preferred corresponding template amino acids are as follows:

TABLE OF CORRESPONDENCE

|  | Macromolecule | Template |
| --- | --- | --- |
| Aliphatic | Ala | Ala, Val, Leu, Ile |
|  | Val | Val |
|  | Leu | Leu |
|  | Ile | Ile |
| Non Polar | Gly | Gly, Ala |
|  | Pro | Pro |
|  | Cys | Cys, Ser, Thr |
|  | Met | Met, Lys, Arg |
| Aromatic | His | His, Trp |
|  | Phe | Phe, Tyr |
|  | Tyr | Tyr |
|  | Trp | Trp |
| Polar | Asn | Asn, Gln |
|  | Gln | Gln |
|  | Ser | Ser, Cys, Thr |
|  | Thr | Thr |
| Charged | Lys | Lys |
|  | Arg | Arg |
|  | Asp | Asp, Glu |
|  | Glu | Glu |

Non-encoded amino acids and/or amino acid analogues that correspond to portions of a polypeptide macromolecule will be apparent to those of skill in the art. In addition, for other types of macromolecules, those of skill in the art will recognize that template molecules can be selected or prepared with topographic substitutions according to the principles discussed above for polypeptide macromolecules. For example, an oligonucleotide macromolecule adenine can be topographically substituted with 7-diazadenine; a macromolecule guanine with 7-diazaguanine; a macromolecule cytosine with 5-methylcytosine, etc. Specific typographic substitutions will depend upon the specific macromolecule and will be apparent to those of skill in the art.

The closeness of the correspondence between the template molecule and the macromolecule of interest will depend upon the desired degree of specificity between the imprint and the target macromolecule. Template molecules that correspond identically to a portion of a macromolecule are expected to exhibit the highest degree of specificity for the macromolecule. Thus, the closeness of correspondence will depend upon, among other factors, the particular application and the complexity of the sample, and will be apparent to those of skill in the art. Preferably, the template molecule will correspond identically to a portion of the macromolecule to be captured.

It has been discovered that the presence of reactive groups such as sulfhydryl groups in template molecules can be disadvantageous for the preparation of molecular imprints. Nevertheless, the imprint compositions of the present invention can be prepared to capture macromolecules that contain such reactive groups. The imprint compositions of the present invention can be prepared so efficiently and inexpensively that a number of techniques can be applied to such macromolecules. To avoid including such reactive groups, a template can be designed that corresponds to a portion of the macromolecule that does not contain the reactive group. However, if a portion of the macromolecule is selected that includes a reactive group, the template molecule can be designed to include a topographic substitution for the reactive group. In particular, macromolecular Cys residues can be substituted to Ser residues in the template molecule. Alternatively, reagents can be used to reduce or block the reactive groups of the macromolecule and of the corresponding template molecule. Such reagents are known to those of skill in the art. For example, any template Cys residue can be reduced with dithiothreitol or P-mercaptoethanol or blocked with reagents that prevent the formation of inter molecular or intramolecular disulfide bridges such as N-ethylmaleimide, iodoacetic acid or other reagents known to those of skill in the art. When the template molecules are "blocked" in this fashion, the reactive groups in the macromolecule to be captured are preferably blocked with the same reagent, as a higher degree of specificity during capture will be achieved. For example, to capture a polypeptide macromolecule which includes disulfide bridges with a molecular imprint prepared with a template molecule in which the Cys residues are blocked, the disulfide bridges of the macromolecule should be reduced prior to, or concomitant with, contacting the macromolecule with the molecular imprint. Preferably, the sulfhydryl groups of the reduced Cys residues will be further blocked with the same reagent used to block the template Cys residues.

Those of skill in the art will also recognize that in many instances compounds that mimic the structures of other compounds are known. The template molecule may comprise, in whole, or in part, such mimetic structures. Mimetic compounds that can be used to create template molecules, as well as their use to create template molecules, will be apparent to those of skill in the art.

For example, peptidomimetic compounds that mimic the structures of peptides are well known. One class of peptidomimetics includes the class of compounds in which the amide linkage of the peptide chain are replaced with isosteres of amides. Isosteres of amide bonds generally include, but are not limited to, $—CH_2NH—$, $—CH_2S—$, $—CH_2CH_2—$, $—CH=CH—$ (cis and trans), $—C(O)CH_2—$, $—CH(OH)CH_2—$ and $—CH_2SO—$. Compounds having such non-amide linkages and methods for preparing such compounds are well-known in the art (see, e.g., Spatola, March 1983, Vega Data Vol. 1, Issue 3; Spatola, 1983, "Peptide Backbone Modifications" In: Chemistry and Biochemistry of Amino Acids Peptides and Proteins, Weinstein, ed., Marcel Dekker, New York, p. 267 (general review); Morley, 1980, Trends Pharm. Sci. 1:463–468; Hudson et al., 1979, Int. J. Prot. Res. 14:177–185 ($—CH_2NH—$, $—CH_2CH_2—$); Spatola et al., 1986, Life Sci. 38:1243–1249 ($—CH_2—S$); Hann, 1982, J. Chem. Soc. Perkin Trans. 1. 1:307–314 ($—CH=CH—$, cis and trans); Almquist et al., 1980, J. Med. Chem. 23:1392–1398 ($—COCH_2—$); Jennings-White et al., Tetrahedron. Lett. 23:2533 ($—COCH_2—$); European Patent Application EP 45665 (1982) CA 97:39405 ($—CH(OH)CH_2—$); Holladay et al., 1983, Tetrahedron Lett. 24:4401–4404 ($—C(OH)CH_2—$); and Hruby, 1982, Life Sci. 31:189–199 ($—CH_2—S—$). The template peptides may include one or more of such amide isosteres or combinations of such isosteres.

Additionally, one or more amide linkages can be replaced with peptidomimetic or amide mimetic moieties which do not significantly interfere with the structure or activity of the peptides. Suitable amide mimetic moieties are described, for example, in Olson et al., 1993, J. Med. Chem. 36:3039–3049. All that is required is that the three dimensional surface of the mimetic template compound have a three dimensional surface with sufficient correspondence to the surface of the mimicked portion of the macromolecule to create a cavity that specifically fits the portion of the macromolecule.

The template molecule may correspond to any portion of the macromolecule, including an internal region, a terminal region, or a modifying molecule such as a polysaccharide of a glycoprotein. Preferably, the portion of the structure of the macromolecule is of sufficient size that the macromolecule forms a tight complex with the molecular imprint. Also preferably, the portion of the macromolecule is sufficiently unique that the molecular imprint is selective for the macromolecule. For instance, if the macromolecule is to be captured from a complex mixture, a preferred template molecule corresponds to a portion of the macromolecule that uniquely defines that macromolecule over other macromolecules in the mixture. Such a unique portion of the macromolecule can be determined by comparing the structure of the macromolecule with the structures of known macromolecules of the complex or by statistical analysis. When the macromolecule is a polypeptide, a template molecule consisting of a sequence of seven amino acids can provide a molecular imprint that is highly selective for the macromolecule.

In general, template molecules can correspond to any portion of the macromolecule, as long as the template does not correspond to the entire macromolecule. If the macromolecule consists of n identifiable structural units, then the portion of the macromolecule to which the template corresponds can consist of from 1 up to (n−1) of those structural units. Preferably, the structural units of the macromolecule to which the template molecule corresponds are contiguous within the primary structure of the macromolecule. If one of skill in the art can identify a terminus or termini in the primary structure of the macromolecule, then a preferred template molecule corresponds to a template that includes a terminus of the macromolecule. Alternatively, the portion of the macromolecule to which the template molecule corresponds can be expressed in size as a fraction of the size of the entire macromolecule. For example, template molecules can correspond to a portion of the macromolecule that consists of from 1% to 5%, from 1 to 10%, from 1 to 15%, from 1 to 20%, from 1 to 25%, from 1 to 30%, from 1 to 35%, from 1 to 40%, from 1 to 50%, from 1 to 60%, from 1 to 70%, from 1 to 80%, from 1 to 90%, from 1 to 95%, or from I to 99% of the structure of the entire macromolecule. Preferably, template molecules have a primary structure that corresponds to a contiguous portion of the primary structure of the macromolecule. If the macromolecule is a polymer, the structure of the template molecule can correspond to a sequence of monomers from the polymer.

In instances where the macromolecule is a polymer, the portion of the polymer to which the template molecule corresponds can also be expressed as a range of monomer units of the polymer. If the polymer consists of n monomer units, then the portion of the polymer, to which the template molecule corresponds, can consist of up to (n−1) monomer units. Alternatively, the portion of the polymer can consist of from 1 to 50 monomer units, from 2 to 40 monomer units, from 3 to 30 monomer units, from 3 to 15 monomer units, from 3 to 10 monomer units, from 4 to 10 monomer units, from 4 to 9 monomer units, from 4 to 8 monomer units, from 4 to 7 monomer units, or from 5 to 7 monomer units. If the polymer is branched, then the portion can be branched or unbranched. Preferably, the portion of the polymer is a contiguous sequence of monomers from the primary structure of the polymer.

If the macromolecule is a polypeptide, the template molecule can correspond to a portion of the polypeptide that consists of a sequence of amino acids selected from the primary sequence of the polypeptide. For instance, if the polypeptide has a length of n amino acids, the portion of the macromolecule to which the template molecule corresponds can consist of up to (n−1) amino acids of the primary structure of the polypeptide. Alternatively, the portion of the polypeptide can consist of a range of amino acids from the primary structure of the polypeptide consisting of from 1 to 50 amino acids, from 2 to 40 amino acids, from 3 to 30 amino acids, from 3 to 15 amino acids, from 3 to 10 amino acids, from 4 to 10 amino acids, from 4 to 9 amino acids, from 4 to 8 amino acids, from 4 to 7 amino acids, or from 5 to 7 amino acids. Preferred portions of the macromolecule are those that consist of a continuous sequence of amino acids from the primary structure of the polypeptide. When the macromolecule is a polypeptide, the preferred template molecule corresponds to the contiguous sequence of seven amino acids at the carboxy terminus of the polypeptide. Template molecules that correspond to the amino-termini are less preferable because polypeptides from biological sources often have heterogeneous modifications at their amino-termini.

When the macromolecule is a polypeptide modified with a polysaccharide, the template molecule can be a polysaccharide having a sequence of saccharides selected from the primary sequence of the polysaccharide. If a contiguous polysaccharide component of the polypeptide contains n saccharide units, then the selected sequence of saccharides can contain up to n saccharides. Alternatively, the selected sequence can contain from 1 to 50 saccharides, 2 to 40 saccharides, 3 to 30 saccharides, 3 to 15 saccharides, 3 to 10 saccharides, 4 to 10 saccharides, 4 to 9 saccharides, 4 to 8 saccharides, 4 to 7 saccharides, or 5 to 7 saccharides. If a polysaccharide component of the polypeptide is branched, the template molecule can also be branched. A preferred template molecule corresponds to a contiguous sequence of saccharide units from the polysaccharide, whether branched or unbranched. The template molecule can also correspond to a hybrid structure selected from the primary structure of polypeptide consisting of at least one amino acid and at least one saccharide.

When the macromolecule is a polynucleotide, the template molecule can be an oligonucleotide having a sequence of nucleotides selected from the primary sequence of the polynucleotide. If the polynucleotide has n nucleotides, then the selected sequence of nucleotides can have a length from 1 to (n−1) nucleotides. Alternatively, the selected sequence can contain from 1 to 50 nucleotides, 2 to 40 nucleotides, 3 to 30 nucleotides, 3 to 15 nucleotides, 3 to 10 nucleotides, 4 to 10 nucleotides, 4 to 9 nucleotides, 4 to 8 nucleotides, 4 to 7 nucleotides, or 5 to 7 nucleotides. Preferably, the selected sequence is a contiguous sequence of nucleotides from the primary sequence of the polynucleotide.

When the macromolecule is any type of polymer, the selected sequence of monomers for the structure of the template molecule can be chosen from an internal region of the polymer or from a terminus of the polymer. If the polymer has unique termini, the sequence of monomers can also be chosen from any terminus of the polymer. If the macromolecule is polypeptide, the preferred template molecule for the present invention corresponds to the sequence of amino acids at the carboxy terminus of the polypeptide.

For macromolecules that are non-polymeric such as, for example, antibiotics, the template molecule preferably corresponds to a structural feature that uniquely identifies the antibiotic. For example, if several antibiotics differ in structure from one another by the identity of a single substituent (e.g., a sugar residue, a lipid moiety, etc.), then a molecular imprint prepared with a template molecule that corresponds to that unique feature can be used to specifically capture that antibiotic from a complex mixture of related antibiotics. For example, the antibiotic amphotericin B (AmB) can be selectively captured from a mixture of AmB and amino sugar derivatives thereof with a molecular imprint prepared with a template that corresponds to the amino sugar moiety of amphotericin.

If mixtures of several distinct macromolecules are to be captured, the template can correspond to a common structural feature. For example, a mixture of AmB and amino sugar derivatives thereof can be captured with a molecular imprint prepared with a template molecule that corresponds to their common polyene core.

Due to their ease of manufacture and their inexpensiveness, such molecular imprints can be used for industrial scale isolation and purification of macromolecules, and have broad-ranging applicability toward the separation of complex mixtures of natural products whose component molecular species have similar physiochemical properties.

5.2.3 Template Molecules Useful for Preparing Imprints that Can Capture Novel Macromolecules In those embodiments above where template molecules correspond to portions of known macromolecules, the molecular imprints of the present invention are most useful for capturing known macromolecules. However, in another important embodiment, the present invention is also useful for capturing, isolating, detecting, and quantifying novel macromolecules. In this embodiment, template molecules that do not necessarily correspond to a portion of a known macromolecule can be used to capture novel macromolecules, even those for which no structural information is known.

A novel macromolecule is a macromolecule for which limited or no structural or functional information is available. If any structural information is available, a molecular imprint can be prepared using a template molecule that corresponds to the portion of the available structural information as described above. The template molecule can also correspond to all of the available structural information. When no structural information is known about a macromolecule, but it is known to be functionally related to a known macromolecule, the template molecule can correspond to a portion of a macromolecule having similar function, the template molecule can correspond to a portion of a macromolecule with similar function, or the template molecule can correspond to a consensus sequence of a family of macromolecules with similar function. In addition, for any novel macromolecule, even one for which no structural or functional information is available, a molecular imprint of a template molecule with a random structure might be able to capture the novel macromolecule. For example, an as yet unidentified macromolecule can be captured, isolated, detected, analyzed, quantified and/or identified from a complex sample with such a molecular imprint.

In the present embodiment of the invention, a template molecule can be a peptide, a polynucleotide, a branched or unbranched polysaccharide, or a mimic or derivative of such molecules. When template molecules with random structures are used, a set of template molecules with random structures is particularly useful. For instance, the complete set of random peptides of a defined length can be used to generate a complete set of molecular imprints complementing the peptide template molecules. This complete set of molecular imprints can be used to screen samples for novel polypeptides.

The size of a template molecule should be appropriate for creating an imprint cavity that can specifically fit a portion of a novel macromolecule. In general, a novel macromolecule can be captured with a molecular imprint of a template molecule with a mass of 100 Da to 5000 Da. If a certain class of macromolecule is targeted, then the structure of that class of macromolecule can be used to design or select the structure of template molecules useful for generating the molecular imprints to capture novel macromolecules of the class. For instance, if the novel macromolecule target could be a polymer, then a template molecule can consist of from 3 to 30 monomer units of the polymer. If the novel macromolecule target could be a polypeptide, then a template molecule can consist of from 3 to 30 amino acids. If the novel macromolecular target could be a polysaccharide, then the template molecule can consist of from 3 to 30 saccharides. If the novel macromolecule target could be a glycosylated polypeptide, than a template molecule can consist of from 3 to 30 amino acids, from 3 to 30 saccharides, or a hybrid structure with from 3 to 30 amino acids or saccharides. If the target macromolecule could be a polynucleotide, then the template molecule can consist of from 3 to 30 nucleotides.

Template molecules of the invention may be synthesized or obtained by virtually any means. For example, the template molecule may be obtained from commercial sources, synthesized using standard solution or solid-phase synthetic schemes and/or isolated from biological samples. For example, oligosaccharide, oligonucleotide and peptide template molecules may be obtained commercially or synthesized according to standard techniques. Template molecules that correspond to complete functional domains of, e.g., polypeptide or polynucleotide macromolecules may be obtained by enzymatic cleavage. For example, Fab template molecules may be obtained by enzymatic cleavage of antibody macromolecules. Double-stranded oligonucleotide template molecules may be obtained by endonucleolytic cleavage of polynucleotide macromolecules. The actual technique used to obtain the template molecule will depend upon the identity of the template molecule, and will be apparent to those of skill in the art.

5.2.4 Formation of an Imprint

The imprint compositions of the invention can be prepared according to any of the known techniques for making molecular imprints, with one important modification. Instead of creating an imprint with the macromolecule to be captured, the imprint compositions of the invention are created with a template molecule. Non-limiting examples of suitable techniques that can be used in conjunction with the invention are described, e.g., in U.S. Pat. Nos. 5,858,296; 5,786,428; 5,587,273; 5,821,311; 5,814,223; and 5,757,717; U.S. Pat. Nos. 5,994,110; 5,959,050; 5,916,445; 5,872,198; 5,814,223; 5,728,296; 5,630,978; and U.S. Pat. No. 5,310,648, the disclosures of which are incorporated herein by reference.

A general method for preparing an imprint composition of the present invention is illustrated in FIG. 2. Referring to FIG. 2, a template molecule 12 is contacted with a matrix material 14 under conditions in which template molecule 12 becomes entrapped or embedded within matrix material 14, yielding complex 16. As illustrated, the template molecule 12 corresponds in structure to an internal portion of a macromolecule 10. Matrix material 14 is a compound or mixture of compounds that is capable of undergoing a change of physical state from a fluid form to a solid or semisolid form. Matrix material 14 may comprise virtually any compound or mixture compounds that is compatible with template molecule 12 and that is capable of undergoing a change of physical state to form a solid or semisolid such that the changed form is capable of retaining shaped cavities. The physical state change can be induced by virtually any means, including by thermal, chemical and/or electromagnetic processes. Examples of suitable compounds are discussed below.

Preferably, the conditions under which the template molecule is imprinted are similar or identical to the conditions under which the macromolecule is to be captured. For instance, if the macromolecule is to be captured under denaturing conditions, then the template molecule should be imprinted under the same denaturing conditions. Similarly, if the macromolecule is to be captured under native conditions, then the template molecule should be imprinted under the same native conditions. Native and denaturing conditions are well-known to those of skill in the art. Particular native and denaturing conditions for capturing certain macromolecules are discussed in detail below.

During the embedding process, matrix material 14 changes physical state from a fluid state to a solid or a semisolid state 14' in the presence of template molecule 12. Fluid states are known to those of skill in the art and include those states where the molecules of matrix material 14 move freely among themselves and where compound 14 retains little or no definite form. In the fluid state, template molecule 12 can mix freely with the molecules of matrix material 14. In the solid or semisolid state, matrix 14' is sufficiently shape-retaining to retain cavities that complement the shape of template molecule 12. Removal of template molecule 12 from complex 16, by, for example, extensive washing, yields imprint composition 18. In imprint composition 18, solid or semisolid matrix 14' defines cavities 12' that complement the topography of template molecule 12. Complex 16 and imprint composition 18 may comprise template molecules 12 that are wholly embedded within matrix 14' and are therefore not removed during the removal step.

Although not illustrated, matrix material 14 can also be contacted with a plurality of different template molecules, each like template molecule 12. Each template molecule can correspond to a portion of a different macromolecule yielding a variation of matrix 14' that can capture a plurality of different macromolecules. Alternatively, each template molecule can correspond to a different portion of the same macromolecule yielding a variation of matrix 14' that can bind or capture the macromolecule at a plurality of positions.

In one embodiment, matrix material 14 may be a solid or semisolid compound that liquifies upon application of heat and resolidifies when the heat is removed. Referring to FIG. 2, to make an imprint composition according to the invention using such a heat sensitive compound, template molecule 12 and heat sensitive compound 14 are mixed under conditions in which heat sensitive compound 14 liquifies. The heat source is then removed and, as the liquid cools, it solidifies to form complex 16. Removal of template molecules 12 via, for example, diffusion, yields imprint composition 18. Of course, in order to maintain the integrity of cavities 12', imprint composition 18 should be kept at temperatures below the liquification temperature of heat sensitive compound 14 during storage and subsequent manipulations.

Many heat-sensitive compounds that can be used to make imprint compositions according to the invention are known in the art and include, by way of example and not limitation, hydrogels such as agarose, gelatins, moldable plastics, etc. Examples of other suitable hydrogels are described in U.S. Pat. Nos. 6,018,033, 5,277,915, 4,024,073, and 4,452,892, the disclosures of which are incorporated herein by reference. Preferably, the temperature at which the heat-sensitive compound 14 liquifies will be in a range that does not destroy or otherwise substantially degrade the template molecule 12.

In another embodiment, matrix material 14 may comprise a compound or mixture of compounds that undergoes a chemical or light induced liquid-to-solid state change. Examples of these types of compounds that are suitable for use with the present invention include, but are not limited to styrene, methyl methacrylate, 2-hydroxyethyl methacrylate, 2-hydroxyethyl acrylate, methyl acrylate, acrylamide, vinyl ether, vinyl acetate, divinylbenzene, ethylene glycol dimethacrylate, ethylene glycol diacrylate, pentaerythritol dimethacrylate, pentaerythritol diacrylate, N,N'-methylenebisacrylamide, N,N'-ethylenebisacrylamide, N,N'-(1,2-dihydroxyethylene)bis-acrylamide, trimethylolpropane trimethacrylate, vinyl cyclodextrin, and polymerizable cyclodextrin. Further examples of polymerizable compounds that are useful for the preparation of molecular imprints can be found in U.S. Pat. No. 5,858,296, which is hereby incorporated by reference in its entirety. The preferred polymerizable substance for the present invention is acrylamide.

Preferably, matrix material 14 comprises a monomer or mixture of monomers that undergo chemical or light-induced polymerization to yield a solid or semisolid polymer matrix ("polymerizable compound"). Referring to FIG. 2, in order to prepare imprint compositions according to the invention with such polymerizable compounds 14, the template molecule 12 and a polymerizable compound 14 are mixed in a solvent that is suitable for polymerization of polymerizable compound 14. If necessary, an initiator for the polymerization of the polymerizable compound is included. Optionally, the template molecule 12 can be covalently bound to the polymerizable compound 14, or the two can be allowed to form non-covalent complexes. Polymerization can by started by adding an appropriate catalyst such as ultraviolet radiation or free radical initiation. After polymerization is complete, the template molecule 12 is removed by diffusion, incubation in a chaotropic reagent such as urea or guanidine, or by other techniques known to those of skill in the art.

Cross-linking reagents can optionally be used with a polymerizable compound 14 to confer rigidity to the molecular imprint. The present invention contemplates any ratio of polymerizable compound to cross-linking reagent that yields a molecular imprint of sufficient integrity to form a cavity whose shape corresponds to the shape of the template molecule. Cross-linking reagents are known to those of skill in the art. Examples of such cross-linking reagents can be found in U.S. Pat. No. 5,858,296. Preferred molecular imprints are prepared with acrylamide and the cross-linking reagent ethylene glycol dimethacrylate (EGDMA) or with acrylamide and bisacrylamide.

In general, matrix material 14 and template molecule 12 can be contacted under any conditions which permit matrix material 14 change physical state to a solid or semisolid matrix 14'. For instance, matrix material 14 and template molecule 12 can be contacted under native conditions or under denaturing conditions. "Native conditions" and "denaturing conditions" can be defined with respect to the template molecule or with respect to the template molecule or with respect to the macromolecule according to principles known to those of skill in the art. Preferably, the conditions of contacting matrix material 14 and template molecule 12 are similar or identical to the conditions of contacting macromolecule 10 and matrix 14'.

The concentration of matrix material 14, template molecule 12, and an optional cross-linking reagent are not critical for success and can be determined according to principles known to those of skill in the art of molecular imprinting. The previously cites references provide guidance for choosing appropriate concentrations for specific matrix materials. The number of cavities 12' in matrix 14' can be adjusted by varying the concentration of template molecule 12. Generally, the concentration of template molecule 12 can vary widely, ranging from as low as 0.01 mM to as high as 1 M. Although the concentration of the template molecule is not critical, template molecule concentrations of about 1 mM produce effective molecular imprints.

Once the matrix is in a solid or semi-solid state, the molecular imprints can be processed to take on a variety of shapes. Usually, the molecular imprint will initially take on the same shape as the container used to create matrix 14'. However, any shape that might be useful for capturing macromolecules is possible. For example, they may be in the form of individual beads, disks, ellipses, or other regular or irregular shapes (collectively referred to as "beads"), or in the form of sheets. Beads can be formed by grinding a rigid matrix 14' or by suspension and dispersion techniques. Methods of making imprinted beads are discussed in Damen et al., 1980, J. Am. Chem. Soc. 102:3265–3267; Braun et al., 1984, Chemiker-Zeitung 108:255–257; and Bystrom et al., 1993, J. Am. Chem. Soc. 115:2081–2083. Imprinted beads may also be prepared by imprinting in the pore network of preformed beaded silica as discussed in Wulff et al., 1985, Reactive Polymers 3:261–2757. Dispersion techniques are discussed in Sellergren et al., 1994, 673:133–141. The formation of beaded molecular imprints by suspension polymerization is described in U.S. Pat. No. 5,821,311. All of these references are incorporated herein by reference.

5.2.5 Formation of a Surface Imprint

In a preferred embodiment, the molecular imprints of the present invention are surface imprints. Surface imprint compositions are molecular imprint compositions in which a substantial number or fraction of the imprint cavities are localized at or near the surface of the imprint. Surface cavities are more accessible to macromolecules and are oriented to facilitate binding. Because of the high density of imprint cavities, surface imprints have greater capacity for binding macromolecules. A detailed description of surface imprints and methods for their preparation are described in copending application Ser. No. 09/507,299, supra, which is hereby incorporated by reference in its entirety. Briefly, surface imprints may be prepared by forming the imprint cavities around an immobilized template molecule. Alternatively, surface imprints can be prepared by a two-phase method. In the two-phase method, a conjugate molecule is prepared that can partition to the interface of two phases. The conjugate molecule comprises a template moiety that constitutes a template molecule as described above and a tail moiety. The template moiety is soluble in one phase of the two phase system, and a matrix material 14 is soluble in the same phase. The tail moiety is soluble in the other phase of the two phase system. When the matrix material changes physical state, a matrix 14' is formed defining oriented surface cavities that complement the shape of the template moiety. These surface imprints can be used in any the methods of the present invention.

5.2.6 Arrays of Imprints

The present invention also provides arrays of imprints and/or imprint compositions. The arrays may be comprised of a plurality of individual imprint compositions arranged in an array or pattern, or may comprise a single piece or sheet of matrix material having a plurality of imprint cavities imprinted thereon. In this latter embodiment, the imprint cavities are arranged in an array or pattern. The arrays may be one-dimensional, two-dimensional or three-dimensional. For instance, if the array comprises individual beads, a one-dimensional array can be prepared by introducing the beads into a capillary tube. A two-dimensional array can be prepared by distributing the beads into the wells of a microtiter plate and/or by affixing the individual beads onto a substrate.

Figure 3A:
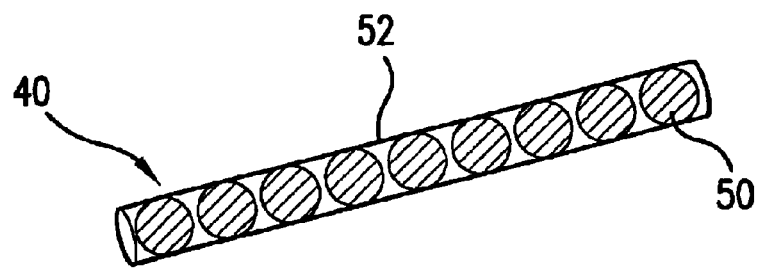
FIG. 3A illustrates a one-dimensional surface imprint array.

For example, referring to FIG. 3A, the array can be an ordered pattern of individual beads 50 where each bead 50 is an imprint composition of the invention. As illustrated in FIG. 3A, the individual beads 50 may be disposed within a housing 52. Housing 52 can serve the dual purpose of retaining the ordering of individual beads 50 and providing a structure through which the sample may be flowed. The ends of the capillary tube may be optionally plugged with, for example, glass wool, a frit, or other porous materials to hold the beads in the tube during sample flow.

Figure 3B:
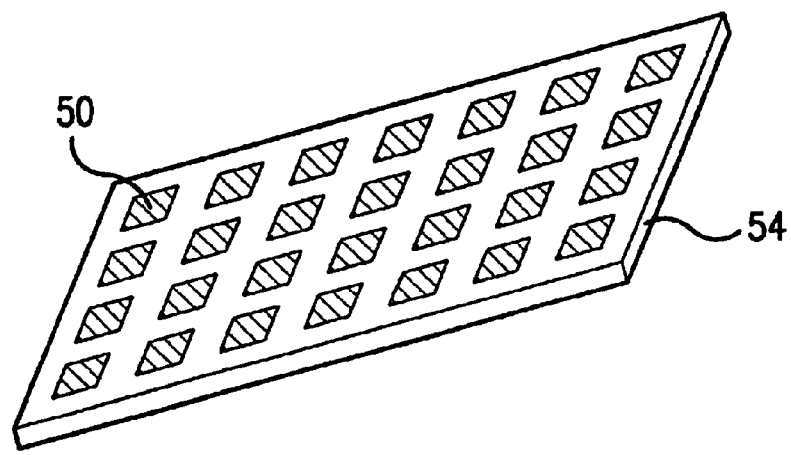
FIG. 3B illustrates a two-dimensional array of surface imprint beads distributed on a substrate.

Alternatively, individual beads 50 could be distributed, either singly or in pluralities, amongst the wells of, for example, a microtiter plate, or affixed to the surface of a substrate, such as a glass plate, plastic sheet or film, etc. For example, referring to FIG. 3B, individual imprints 50 (in this case illustrated as square pads) can be affixed onto a glass sheet 54 in an ordered two-dimensional matrix. Methods for fixing polyacrylamide pads that can be adapted to create arrays according to the invention are described in U.S. Pat. No. 5,552,270. Methods of affixing other types of matrix materials onto substrates are well-known and will be apparent to those of skill in the art.

As illustrated by the above examples, a key feature of the arrays of the invention is the ability to correlate the identity of a particular imprint with its relative position within the array. The identity of an imprint is defined by the identity of the template molecule used to create the imprint. Thus, in the array illustrated in FIG. 3B, the identity of a particular imprint 50 is identifiable by its xy-coordinates within the array. In the array illustrated in FIG. 3A, the identity of a particular imprint 50 is identifiable by its x-coordinate within the array. This feature is particularly useful for detecting, capturing, analyzing, isolating and/or quantifying pluralities of macromolecules from complex samples, as will be discussed in more detail, below.

Figure 3C:
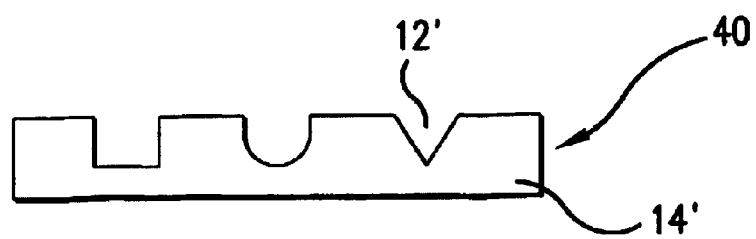
FIG. 3C illustrates a cross-sectional view of an embodiment of a surface imprint array.

The arrays of the invention also include matrices which have pluralities of imprint cavities disposed at defined relative positions. For example, referring to FIG. 3C, a single sheet of matrix material 14' may comprise an ordered arrangement of imprint cavities 12'.

In the arrays of the invention, each array element or address (i.e., each set of array coordinates) may be unique, i.e., each address in the array may contain an imprint of a different template molecule, or alternatively, the array may comprise redundancies. Moreover, while in many instances each array element will comprise imprint cavities of a single template molecule, one or more of the array elements may comprise imprint cavities of 2 or more different template molecules.

The number of elements comprising the array can vary over a wide range, from as few as 2 to as many as 10, $10^2$, $10^3$, $10^4$, $10^5$, $10^6$ or even more, and is limited only by the ability to make an array having the desired complexity, as will be described in more detail, below.

Figure 4:
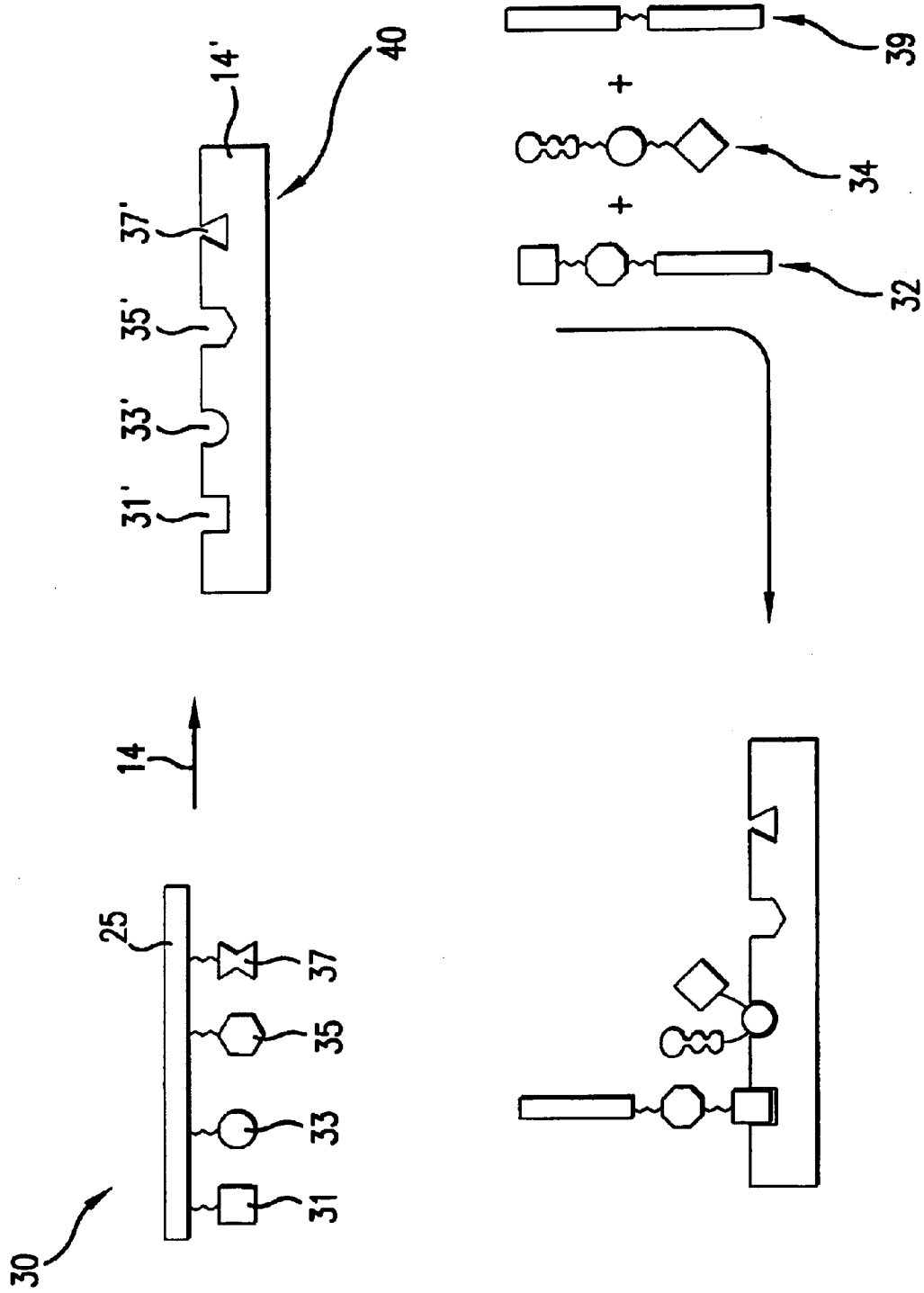
FIG. 4 illustrates the capture of a plurality of macromolecules with one embodiment of a molecular imprint array.

The spatially identifiable arrays of the invention provide the ability to screen and/or analyze complex samples. For example, referring to FIG. 4, imprint array 40 is constructed from template array 30. Template array 30 comprises a plurality of template molecules 31, 33, 35 and 37 which uniquely correspond to macromolecules 32, 34, 36 and 38, respectively. Imprint array 40 comprises matrix 14' which defines cavities 31', 33', 35' and 37' which correspond to template molecules 31, 33, 35 and 37, respectively. Because template array 30 is spatially identifiable (i.e., the identities of the template molecules are known or identifiable by their coordinates or relative positions within the array), imprint array 40 is also spatially identifiable. Moreover, since the template molecules uniquely correspond to their respective macromolecules, imprint array 40 can be used to detect the presence of macromolecules 32, 34, 36 and 38 in a sample. For example, referring to FIG. 4, imprint array 40 is contacted with a sample comprising macromolecules 32, 34 and 39 under conditions in which the macromolecules bind, or become captured by, their respective imprint cavities. Macromolecules 32 and 34 are captured at locations corresponding to cavities 31' and 33'. When the array is scanned for bound macromolecules, the presence of macromolecules at the addresses corresponding to templates 31 and 33 reveals that the sample contained macromolecules 32 and 34. Macromolecule 39 is not detected, as imprint array 40 does not contain an address or element capable of binding this macromolecule. The relative amounts of macromolecules 32 and 34 in the sample can be optionally determined by quantifying the amount of captured macromolecules at each address, as will be described in more detail below.

A spatially identifiable array of molecular imprints is particularly useful when an array of molecular imprints of template molecules that do not necessarily correspond to portions of known macromolecules is used to screen a complex mixture in order to isolate novel macromolecules. Partial structural information about any captured novel macromolecule can be deduced from the position at which it binds the array. In order for capture to occur, a portion of the captured novel macromolecule must have a structure that corresponds to the structure of the template molecule that was used to create the imprint at that position in the array. If the captured, novel macromolecule is a protein and the molecular imprint is an imprint of a peptide template molecule, then a portion of the amino acid sequence of the captured macromolecule might even be identical to the amino acid sequence of the peptide template molecule.

5.2.7 Methods of Making Arrays

The arrays of the invention can be readily prepared using standard techniques available in the art. Arrays comprised of individual imprint beads may be prepared by any method of dispensing and/or affixing the beads in a spatially defined fashion known in the art. The imprint beads are prepared according to the previously described methods.

Arrays comprised of a single piece or sheet of matrix are typically prepared using an array of immobilized template molecules. The array of template molecules can be prepared according to any of the techniques well-known to those of skill in the art. For example, an array of immobilized template molecules may be prepared by synthesizing each template molecule on an individual synthesis substrate such as a glass bead or other solid-phase synthesis resin and affixing the individual synthesis substrates to another substrate such as a glass or plastic sheet or film in an ordered array or pattern without cleaving the template molecules from the synthesis substrates. Such substrates of immobilized template molecules may be prepared individually, or pluralities of different immobilized template molecules may be prepared simultaneously using one of the numerous combinational synthesis strategies known in the art (see, e.g., U.S. Pat. Nos. 6,001,579; 5,968,736; 5,961,923; 5,925,562; 5,789,172; Fodor et al., 1991, Science 251:767–773; Brenner and Lerner, 1992, Proc. Natl. Acad. Sci. USA 81:5381–5383; Amoto, 1992, Science 257:330–331; Lam et al., 1991, Nature 354:82–84; Houghton et al., 1991, Nature 354:84–86; Jung and Beck-Sickinger, 1992, Angew. Chem. Int. Ed. Engl. 91:367–383; and Kerr et al., 1993, J. Amer. Chem. Soc., 115:2529–31).

Methods for making myriad different types of immobilized template molecules are well-known. For example, methods for synthesizing peptide template molecules immobilized on synthesis substrates are described in Merrifield, 1997, Meth. Enzymol. 289:3–13; methods for synthesizing oligonucleotide template molecules immobilized on synthesis substrates are described in Southern et al., 1994, Nuc. Acids Res. 22:1368–1373. A plethora of reactions available for synthesizing a wide variety of other types of immobilized template molecules are described in Bunin, 1998, The Combinational Index, Academic Press, San Diego, Calif. Alternatively, the arrays of the invention may be prepared from an array of template molecules in which each template molecule is immobilized to the same substrate.

Such template arrays can be prepared according to well-known techniques. For example, the template array may be prepared by spotting template molecules onto a substrate under conditions in which the template molecule covalently or non-covalently attached to the substrate using any of the spotting devices described in U.S. Pat. Nos. 5,601,980, 6,001,309, 5,785,926, and 4,877,745. Any of these devices, or other devices useful for dispensing small aliquots of liquids into substrates, can be adapted for use to create the desired array of template molecules.

Alternatively, the array of template molecules may be prepared by synthesizing in situ each template molecule at its desired address or location within the array. Several in situ synthesis methods useful for making arrays of template molecules have been described in the art. For instance, an array of peptides immobilized on a substrate can be prepared according to, for example, U.S. Pat. Nos. 5,958,703; 5,919,523; 5,847,105; or 5,744,305. An array of oligonucleotides immobilized on a substrate can be prepared according to, for example, U.S. Pat. Nos. 5,919,523; 5,843,655, 5,143,854; 5,847,105; 5,837,832; 5,770,722; PCT application No. WO 92/10092; or PCT application No. WO 90/15070.

A significant advantage of preparing the arrays of the invention from template arrays is the dimensions that can be achieved. Template arrays prepared by spotting or in situ synthesis methods can readily be prepared that have synthesis spots or features on the order of 10–100 $\mu$m, permitting the synthesis of tens of thousands, or even millions, of different template molecules in a substrate area measuring about 1 cm on each edge (see, e.g., Fodor et. al., 1991, supra). Imprint arrays created with such template arrays will have similar dimension and complexities. Thus, imprint arrays capable of capturing tens of thousands, hundreds of thousands or even millions of unique macromolecules that measure only 1 cm$^2$ can be readily prepared. The ability to create such miniature array imprints makes it possible, for the first time, to analyze the plethora of macromolecules present in complex samples such as cells. Due to their miniature dimensions, very little sample is required for analysis. Moreover, since template arrays of different types of template molecules can be prepared (e.g., an array comprising both peptide and oligonucleotide template molecules), different types of macromolecules can be captured and analyzed simultaneously.

In instances where the array is prepared with an array of immobilized template molecules, the template molecules can be optionally attached to the support via a labile linkage. The array of molecular imprints can then be prepared by forming imprints, according to one of the methods described above, in the presence of the array of immobilized template molecules. The template molecules can be cleaved from the support prior to removing the support from the newly formed molecular imprints. Cleavable linkages can be cleaved with chemicals, enzymes, or electromagnetic radiation. If the linkage can be cleaved with electromagnetic radiation and the transition of matrix material 14 can also be induced by electromagnetic radiation, the wavelength of the radiation that cleaves the linkage should be compatible with the wavelength of the radiation that induces the transition of the matrix material. Cleaving a labile linker allows the template molecules to be removed from the molecular imprints, according to one of the methods described above, with minimal disruption of the integrity of the molecular imprints. The remaining portions of the template molecules can be removed by diffusion or by incubation in a chaotropic reagent such as urea or guanidine or by other techniques known to those of skill in the art for disrupting molecular complexes. Cleavable linkers and/or linkages suitable for attaching template molecules are known to those of skill in the art. Appropriate examples are described, for instance, in U.S. Pat. Nos. 5,766,556; 5,095,084; 6,013,440; 5,962,337; and 5,958,703, the disclosures of which are hereby incorporated by reference.

5.2.8 Methods of Capturing Macromolecules

Also within the scope of the present invention are methods of using molecular imprints to capture macromolecules. Molecular imprints useful for capturing macromolecules can are prepared as described above. To capture a macromolecule, the macromolecule or a mixture comprising the macromolecule is contacted with the molecular imprint under conditions in which the macromolecule binds the imprint. A macromolecule "binds" a cavity if it becomes entrapped or immobilized within the cavity in a specific manner such that it is specifically captured from a composition comprising it. Preferably, the molecular imprint is an imprint of a template molecule that corresponds to a portion of the macromolecule. For capture, the imprint compositions may be disposed within a housing to create a chromatography column, or used batch-wise. Alternatively, the imprint is an imprint of a template molecule that does not necessarily correspond to a portion of a known macromolecule. An imprint of such a template molecule is useful for capturing a macromolecule whose structure has yet to be determined.

Also preferably, the conditions for contacting the macromolecule with the imprint are similar to or identical to the conditions under which the imprint was formed. While not intending to be bound by any particular theory, it is believed that the molecular imprints of the present invention capture macromolecules because the portion of the macromolecule that corresponds to the template is captured by the cavity of the imprint that formed around the template molecule. If the capture conditions are similar to the imprinting conditions, the portion of the macromolecule is more likely to adopt a structure similar to the structure of the corresponding template molecule.

The choice of conditions depends on the macromolecule and the template molecule that corresponds to a portion of the macromolecule. When the macromolecule is a protein and the template molecule corresponds to sequence of amino acids of the protein, the preferred capture conditions are often denaturing. However, when a template molecule corresponds to a large fragment of a protein, such as a pepsin fragment of an immunoglobulin, then native imprinting and capture conditions will often yield superior results. When the macromolecule is a double-stranded polynucleotide, the preferred capture conditions are native conditions that allow the macromolecule to maintain its native structure. When the macromolecule is a single-stranded polynucleotide, the capture conditions may be native or denaturing conditions. One of skill in the art will recognize whether native or denaturing conditions are appropriate. In situations where the choice of imprinting and capture conditions is not clear, the molecular imprint compositions of the present invention can be prepared so efficiently and inexpensively that a series of conditions can be assayed to determine the ideal conditions.

The exact conditions to retain a native or denatured structure are well-known and will be apparent to those of skill in the art. For instance, denaturing conditions for polypeptides can include SDS, urea, guanidine, or any other protein denaturant known to those of skill in the art. Denaturing conditions for polynucleotides can include high temperature, formamide, high ionic strength, and other conditions known to those of skill in the art.

A plurality of macromolecules can be captured simultaneously by contacting the macromolecules with an array of the invention. The amount of a macromolecule in a sample can be quantified by capturing the macromolecule with a molecular imprint and determining the amount of the macromolecule captured by the imprint. Techniques for detecting a captured macromolecule or quantifying the amount of a captured macromolecule include infrared spectroscopy, UV spectroscopy, visible spectroscopy, surface acoustic wave devices, refractive index, evanescent wave sensors, bulk acoustic wave devices, capacitance measurements, radioimmunoassay measurements, radiolabeling, chemiluminescence measurements, Lamb-wave measurements, fluorescence measurements, Wilhelmy balance, chemiresistor measurements, electrochemical sensors, enzyme-linked immunosorbent assay, resistance, capacitance, acoustic wave, surface plasmon resonance, scanning tuneling microscopy, atomic force microscopy, scanning electron microscopy and other techniques known to those of skill in the art for detecting or quantifying macromolecules such as those described in U.S. Pat. Nos. 5,306,644; 5,313,264; 5,955,729; and 5,976,466.

In one representative embodiment, captured macromolecules can be detected or quantified by measuring the change in ultraviolet absorbence of the array of imprints before and after capture. Alternatively, the change in resistance or capacitance of the array before and after capture can be used to detect captured macromolecules or quantify the amount of captured macromolecules. In another embodiment, a plurality of macromolecules can be radioactively labeled by covalent modification with a radioactive reagent or by synthesizing the macromolecules from radioactively labeled precursors. Captured macromolecules can then be detected or quantified by counting radioactive emissions from the array by techniques well-known to those of skill in the art.

The relative amounts of a plurality of different macromolecules can be quantified by capturing the plurality of macromolecules and quantifying the amount of each macromolecule of the plurality bound to the imprints. In a preferred embodiment, the identity of each imprint is determinable from its relative position within the array. An array of imprints wherein the identity of each imprint is determinable can be prepared from an array of template molecules wherein the identity of each template molecule is determinable from its relative position within the array. Methods of preparing such arrays of template molecules are known to those of skill in the art, such as those described above.

An array of molecular imprints according to the present invention is useful for determining the relative amounts of macromolecules from a complex biological source. This embodiment of the invention specifically encompasses the evaluation of an expression profile of a cell. In this embodiment, the complex mixture of macromolecules comprises a plurality of polypeptides from a cell. An array of imprints is prepared using template molecules that correspond to portions of the polypeptides of the plurality. The plurality of macromolecules is contacted with the array of imprints. The absolute or relative amount of each macromolecule captured by the array of imprints is determined by a method of quantifying polypeptides known to those of skill in the art. For example, the cell that is the source of the plurality of polypeptides can be grown in the presence of radioactively labeled amino acids. The amount of each polypeptide bound by the array can then be determined by scintillation counting or by photographic exposure and densitometry. Alternatively, if antibodies are available for the polypeptides of the plurality, the amount of the polypeptides bound by the array of imprints can be determined by ELISA methods or other methods known to those of skill in the art. If each imprint of the array is on a discrete matrix, then the amount of each bound polypeptide can be determined directly by a protein assay known to those of skill in the art such as the assay described in Lowry et al., 1951, J. Biol. Chem. 193: 265–220, or the assay described in Bradford, 1976 Anal. Biochem. 72: 248–254. The expression profile of the polypeptides of the plurality can be derived from the relative amounts of each polypeptide of the plurality that is bound by the array of imprints.

A macromolecule can be isolated by capturing the macromolecule with a molecular imprint and then recovering the macromolecule from the imprint. The molecular imprint can be an imprint of a template molecule corresponding to a portion of the macromolecule. Alternatively, if the macromolecule has a structure yet to be determined, the imprint can be an imprint of a template molecule that does not necessarily correspond to a portion of a known macromolecule. The macromolecule can be recovered from the imprint by diffusion or by incubation in urea, guanidine, SDS, or other techniques known to those of skill in the art for disrupting macromolecular complexes or for denaturing macromolecules.

5.2.9 Methods of Screening Macromolecules of Unknown or Undetermined Structure

In another aspect, the present invention is drawn to methods of screening macromolecules. This aspect of the invention encompasses screening both macromolecules of determined structure and screening of those of undetermined structure. To screen a plurality of macromolecules, the plurality is contacted with an array of imprints, or imprint compositions, as previously described.

At least one imprint of the array is a molecular imprint of a template molecule as defined above. If the macromolecules to be screened are polypeptides, the template molecule should be a peptide or a polysaccharide. If the macromolecules to be screened are polynucleotides, the template molecule should be a polynucleotide. If the macromolecules to be screened are polysaccharides, the template molecule should be a polysaccharide. If the macromolecules to be screened are a mixture of different classes of macromolecules, the array of imprints can comprise imprints of template molecules of the corresponding classes.

A sample containing a plurality of macromolecules is contacted with the array of imprints. If any macromolecule of the sample contains a structure that corresponds sufficiently to the structure of the template molecule, the macromolecule will be captured by the array of imprints. Any macromolecules captured can be quantified or recovered from the imprint. In instances where the template molecules have structures that do not correspond to any portion of the structure of any known macromolecule, the present method of screening can be used to capture, isolate, analyze, detect, quantify and/or identify novel macromolecules from complex samples.

6. EXAMPLE 1

Preparation of an Imprint of the C-terminal Sequence of Cytochrome c

In this Example, we describe the preparation of an imprint that will bind the protein cytochrome c. The imprint was prepared using as a template molecule the primary sequence of the carboxy-terminus of the polypeptide chain.

To prepare the imprint, a template molecule was constructed that corresponds in sequence to the carboxyterminal portion of the cytochrome c polypeptide. The last seven amino acids of the horse heart cytochrome c polypeptide (Sigma) have the sequence LKKATNE (SEQ ID NO:1). An N-terminal acylated peptide was synthesized with the sequence LKKATNE (SEQ ID NO:1) by standard techniques. An ethylene glycol dimethylacrylate (EDGMA) solution was prepared by dissolving 2 g EDGMA and 0.4 g acrylamide in 3 ml acetonitrile. 20 mg LKKATNE (SEQ ID NO:1) peptide was added to the EDGMA solution. After 20 mg 2,2'-azobisisobutyronitrile (AIBN) was added as a catalyst, the solution was saturated with nitrogen for 5 min and polymerized under ultraviolet irradiation at 370 nm for 12 h at 4° C. The resulting imprint polymer was grounded and washed with three changes of 10% acetic acid in methanol for 24 h and then washed with methanol for 3 h and then three times with water for 1 h each. The ratio of wash volume to polymer volume was 1:1 for all washes.

7. EXAMPLE 2

Capture of Cytochrome c With an Imprint of its C-terminal Sequence

In this Example we demonstrate that a molecular imprint of a peptide having the sequence of the carboxy-terminus of cytochrome c selectively captures the cytochrome c protein from a mixture of proteins.

A protein solution was prepared containing 0.1 mg/ml cytochrome c, 0.1 mg/ml trypsin inhibitor, and 0.1 mg/ml carbonic anhydrase (see FIG. 5, lane 1). 0.15 ml of the protein solution was incubated with 0.1 ml of the imprint polymer described in Example 1 at room temperature overnight. 0.15 ml of the protein solution was also incubated with a control polymer prepared according to the protocol of Example 1 without the addition of a template molecule.

Both the control polymer and the imprint polymer nonspecifically bound a significant amount of all of the proteins (see FIG. 5, lanes 3 and 4). Washing with water failed to elute a significant amount of any of the nonspecifically bound proteins (see FIG. 4, lanes 5 and 6). Washing the control polymer with 2% acetic acid removed almost all of the proteins (see FIG. 5, lane 8). In contrast, washing the imprint polymer with 2% acetic acid removed significant amounts of carbonic anhydrase and trypsin inhibitor only (see FIG. 5, lane 7). Washing with 2% acetic acid removed trypsin inhibitor and carbonic anhydrase from the imprint polymer (see FIG. 5, lane 7), but cytochrome c remained tightly bound to the imprint polymer which retained an orange color. Washing with 2% acetic acid removed all three proteins, including cytochrome c, from the control polymer (see FIG. 5, lane 8).

This Example demonstrates that a imprint of a template molecule selectively and tightly binds the macromolecule corresponding to the template molecule. Other macromolecules were not bound by the imprint, and the cavities formed by the template molecule associate with the macromolecule to form a complex strong enough to withstand 2% acetic acid.

8. EXAMPLE 3

Preparation of a Conjugate Molecule Comprising a Template Molecule Corresponding to the Carboxyterminus of Cytochrome c and a Palmitic Acid Tail Molecule To create a surface imprint capable of binding the protein cytochrome c, a conjugate molecule corresponding in structure to the seven carboxy-terminal amino acids of cytochrome c was constructed. A template molecule was first designed having the amino acid sequence of the seven carboxy-terminal amino acids of the horse heart cytochrome c polypeptide, LKKATNE (SEQ ID NO:1). A seven amino acid sequence should be sufficiently unique to provide a surface imprint with specificity for cytochrome c. A peptide with the sequence LKKATNE (SEQ ID NO:1) was synthesized by standard techniques.

A conjugate molecule was then prepared with the LKKATNE (SEQ ID NO:1) template molecule. Since LKKATNE (SEQ ID NO:1) is a hydrophillic template molecule (see Kyte & Doolittle (1982), J. Mol. Biol. 157:105–132), palmitic acid was chosen as a hydrophobic tail molecule. Palmitic acid was linked to the amino-terminus of the LKKATNE (SEQ ID NO:1) via an amide bond to form a palmitoyl-peptide conjugate molecule.

9. EXAMPLE 4

Preparation of an Acrylamide Surface Imprint Capable of Binding Cytochrome c In this example, we demonstrate the preparation of an acrylamide surface imprint capable of binding cytochrome c. The surface imprint is prepared in a two-phase system with the conjugate molecule of Example 3 whose structure corresponds to the amino acid sequence of the carboxy-terminus of cytochrome c. The conjugate molecule, with a hydrophillic template molecule linked to a hydrophobic tail molecule, was designed to partition to the interface of the two-phase system.

Acrylamide monomer solution was prepared by dissolving 28.5 g acrylamide and 1.5 g N-N'-methylene bisacrylamide in 100 ml of 4 M urea. 2 mg of the palmitoyl-peptide conjugate molecule of Example 1 was dissolved in 1 ml of the acrylamide monomer solution. Ammonium persulfate and TEMED were added to the solution as catalysts. The final concentration of ammonium persulfate was 0.02%, and the final concentration of TEMED was 0.1%. 0.5 ml light mineral oil was added, and the mixture was sonicated at 60 watts for 10 min. The resulting suspension was centrifuged at 5,000×g for 10 minutes to separate phases. After polymerization at room temperature, the mineral oil phase was removed and the polymer was washed with 10 mM Tris-HCl, pH 9.0, containing 4 M urea and 10% SDS for 24 h. The resulting matrix had the form of the interior of an Eppendorf tube.

A control polymer was prepared by the same protocol using a control conjugate molecule prepared with a control template molecule corresponding to a portion of rabbit skeletal muscle myosin heavy chain. The amino acid sequence of the control template molecule, TKVISEE (SEQ ID NO:2), is not found in the primary amino acid sequence of horse heart cytochrome c. A palmitic acid tail molecule was linked to the amino terminus of the control template molecule via an amide bond to generate the control conjugate molecule.

10. EXAMPLE 5

Capture of Cytochrome c with a Polyacrylamide Surface Imprint of its C-terminal Sequence In this example we demonstrate that the acrylamide surface imprint prepared in Example 4 with a seven amino acid template molecule selectively binds the full-length cytochrome c protein.

A 100 μl solution of 0.1 mg/ml bovine serum albumin, 0.1 mg/ml trypsin inhibitor, and 0.1 mg/ml cytochrome c (see FIG. 6, lane 1) in MES/urea buffer (10 mM MES, pH 5.0, and 4 M urea) was incubated with approximately 0.5 cm$^2$ surface imprint of Example 4 at room temperature for 4 h.

A 100 μl sample of the same protein solution was also incubated with a control polymer prepared according to the protocol of Example 4 with the control conjugate molecule corresponding to rabbit myosin heavy chain (see FIG. 6, lanes 3 and 5). The supernatant was removed (see FIG. 6, lanes 2 and 3) and the surface imprint was washed twice with 500 ml MES/urea buffer for 15 min each. Proteins were eluted by washing overnight with 10% SDS in MES/urea buffer (see FIG. 6, lanes 4 and 5).

The supernatant from the surface imprint incubation (see FIG. 6, lane 2) shows significantly more cytochrome c bound the surface imprint compared to the amount bound by the control polymer (see FIG. 6, lane 3). Washing with MES/urea buffer removed non-specifically bound proteins from the surface imprint and from the control polymer. Elution overnight with 10% SDS removed a fraction of the cytochrome c specifically bound to the surface imprint (see FIG. 6, lane 4) and some non-specifically bound BSA (see FIG. 6, lanes 4 and 5).

This example demonstrates that the surface imprints of the present invention can be used to specifically capture and isolate a protein from a mixture of proteins. This example also demonstrates that the capture of cytochrome c depends on the structure of the template molecule. The control polymer imprinted with a template molecule that has no correspondence to cytochrome c showed no specific binding of cytochrome c (see FIG. 6, lane 5).

11. EXAMPLE 6

Preparation of an Acrylamide Surface Imprint Capable of Binding Cytochrome c In this example, we demonstrate the preparation of a second acrylamide surface imprint capable of binding cytochrome c. The surface imprint is prepared in a two-phase system with the conjugate molecule of Example 3 whose structure corresponds to the amino acid sequence of the carboxy-terminus of cytochrome c. The conjugate molecule, with a hydrophillic template molecule linked to a hydrophobic tail molecule, was designed to partition to the interface of the two-phase system.

Acrylamide monomer solution was prepared by dissolving 28.5 g acrylamide and 1.5 g N-N'-methylene bisacrylamide in 100 ml of 4 M urea. 2 mg of the palmitoyl-peptide conjugate molecule of Example 1 was dissolved in 1 ml of the acrylamide monomer solution. Ammonium persulfate and TEMED were added to the solution as catalysts. The final concentration of ammonium persulfate was 0.02%, and the final concentration of TEMED was 0.1%. 0.5 ml light mineral oil was added, and the mixture was sonicated at 60 watts for 4 min. The resulting suspension was centrifuged at 5,000× g for 10 minutes to separate phases. After polymerization at room temperature, the mineral oil phase was removed and the polymer was washed with 10 mM Tris-HCl, pH 9.0, containing 4 M urea and 10% SDS for 24 h. The resulting matrix was ground into beads approximately 0.1 mm in diameter.

12. EXAMPLE 7

Capture of Cytochrome c with a Polyacrylamide Surface Imprint of its C-terminal Sequence In this example we demonstrate that the acrylamide surface imprint prepared in Example 6 with a seven amino acid template molecule selectively binds the full-length cytochrome c protein.

A 100 μl solution of 0.1 mg/ml bovine serum albumin, 0.1 mg/ml trypsin inhibitor, and 0.1 mg/ml cytochrome c (see FIG. 7, lane 1) in MES/urea buffer (10 mM MES, pH 5.0, and 4 M urea) was incubated with approximately 1.5 cm$^2$ surface imprint of Example 6 at room temperature for 4 h. A 100 μl sample of the same protein solution was also incubated with a control polymer prepared according to the protocol of Example 6 with no conjugate molecule (see FIG. 7, lanes 1 and 3). The supernatant was removed (see FIG. 7, lanes 1 and 2) and the surface imprint was washed twice with 500 ml MES/urea buffer for 15 min each. Proteins were eluted by washing overnight with 10% SDS in MES/urea buffer (see FIG. 7, lanes 3 and 4).

The supernatant from the surface imprint incubation (see FIG. 7, lane 2) shows significantly more cytochrome c bound the surface imprint compared to the amount bound by the control polymer (see FIG. 7, lane 1). Washing with MES/urea buffer removed non-specifically bound proteins from the surface imprint and from the control polymer. Elution overnight with 10% SDS removed a significant fraction of the cytochrome c specifically bound to the surface imprint (see FIG. 7, lane 4) and some non-specifically bound BSA (see FIG. 6, lanes 3 and 4).

This example further demonstrates that the surface imprints of the present invention can be used to specifically capture and isolate a protein from a mixture of proteins.

13. EXAMPLE 8

Capture of Cytochrome c from a Cell Lysate With a Polyacrylamide Surface Imprint of its C-terminal Sequence In this example we demonstrate that the acrylamide surface imprint prepared in Example 6 with a seven amino acid template molecule selectively binds the full-length cytochrome c protein from a complex cell lysate.

A 100 μl solution of a cell lysate (1 mg total protein from rat pheochromocytoma cells) spiked with 0.1 mg/ml cytochrome c in MES/urea buffer (10 mM MES, pH 5.0, and 4 M urea) was incubated with approximately 1.5 cm$^2$ surface imprint of Example 6 at room temperature for 4 h. A 100 μl sample of the same protein solution was also incubated with a control polymer prepared according to the protocol of Example 6 with no conjugate molecule (see FIG. 7, lanes 5 and 7). The supernatant was removed (see FIG. 7, lanes 5 and 6) and the surface imprint was washed twice with 500 ml MES/urea buffer for 15 min each. Proteins were eluted by washing overnight with 10% SDS in MES/urea buffer (see FIG. 7, lanes 7 and 8).

The supernatants from both surface imprint compositions showed that most proteins of the cell lysate did not bind the compositions (see FIG. 7, lanes 5 and 6). Washing with MES/urea buffer removed non-specifically bound proteins from the surface imprint and from the control polymer. Elution overnight with 10% SDS removed a fraction of the cytochrome c specifically bound to the surface imprint (see FIG. 7, lane 8). The control imprint did not specifically bind cytochrome c (see FIG. 7, lane 7).

This example demonstrates the powerful specificity of the surface imprints of the present invention. The surface imprint of the carboxy-terminus selectively bound cytochrome c from a complex cell lysate. Surface imprints of the present invention can be used to capture and isolate specific macromolecules from the most complex mixtures of biological macromolecules.

The present invention is not to be limited in scope by the exemplified embodiments, which are intended as illustrations of single aspects of the invention, and any compositions and methods which are functionally equivalent are within the scope of the invention. Indeed, various modifications of the invention in addition to those described above will become apparent to those skilled in the art from the foregoing description and accompanying drawings. Such modifications are intended to fall within the scope of the appended claims.

All patents and publications cited herein are hereby incorporated by reference in their entirety.

What is claimed is:

1. An imprint composition comprising a matrix, said matrix defining an imprint cavity of a template molecule that corresponds to a portion of a macromolecule of interest.

2. The imprint composition of claim 1 in which the matrix material comprises a polymer.

3. The imprint composition of claim 2, wherein the polymer comprises a polymerized monomer selected from the group consisting of styrene, methyl methacrylate, 2-hydroxyethyl methacrylate, 2-hydroxyethyl acrylate, methyl acrylate, acrylamide, vinyl ether, vinyl acetate, divinylbenzene, ethylene glycol dimethacrylate, ethylene glycol diacrylate, pentaerythritol dimethacrylate, pentaerythritol diacrylate, N,N'-methylenebisacrylamide, N,N'-ethylenebisacrylamide, N,N'-(1,2-dihydroxyethylene)bisacrylamide and trimethylolpropane trimethacrylate.

4. The imprint composition of claim 1 in which the matrix material comprises a heat-sensitive compound.

5. The imprint composition of claim 4 in which the heat-sensitive compound is selected from the group consisting of hydrogels, agarose, gelatins and moldable plastics.

6. The imprint composition of claim 1, wherein the template molecule corresponds to a terminal portion of the macromolecule.

7. The imprint composition of claim 1, wherein the macromolecule is a polynucleotide and the template molecule is an oligonucleotide.

8. The imprint composition of claim 1, wherein the macromolecule is a polypeptide and the template molecule is an oligosaccharide.

9. The imprint composition of claim 1, wherein the macromolecule is a polypeptide and the template molecule is a peptide.

10. The imprint composition of claim 9, wherein the sequence of the peptide corresponds to a contiguous sequence of the polypeptide.

11. The imprint composition of claim 10, wherein the peptide is between 3 and 30 amino acids in length.

12. The imprint composition of claim 10, wherein the peptide is between 4 and 15 amino acids in length.

13. The imprint composition of claim 10, wherein the peptide is between 4 and 7 amino acids in length.

14. The imprint composition of claim 10, wherein the portion of the polypeptide comprises the C-terminus of the polypeptide.

15. The imprint composition of claim 1 further including the macromolecule, wherein the macromolecule is bound or associated with an imprint cavity.

16. An imprint composition comprising a matrix, said matrix defining a plurality of imprint cavities of a plurality of template molecules, wherein at least two of the template molecules are unique.

17. The imprint composition of claim 16 in which least one template molecule is a molecule that corresponds to a portion of a macromolecule of interest.

18. The imprint composition of claim 16 in which each template molecule of the plurality is unique.

19. The imprint composition of claim 16 in which the plurality of imprint cavities are arranged in a spatially identifiable pattern or array.

20. The imprint composition of claim 16 in which each template molecule is a peptide of from 3 to 7 amino acids in length.

21. The imprint composition of claim 16 in which the plurality of template molecules comprises the complete set of peptides of 7 amino acids in length.

22. A plurality of imprint compositions according to claim 1.

23. The plurality of claim 22, in which at least two compositions of the plurality are unique.

24. The plurality of claim 22, in which each composition defines imprint cavities of at least two different template molecules.

25. The plurality of claim 24, wherein each different template molecule corresponds to a different portion of the same macromolecule.

26. The plurality of claim 24, wherein each different template molecule corresponds to a different macromolecule.

27. The plurality of claim 22, wherein the compositions are arranged in a spatially-identifiable array or pattern.

28. The plurality of claim 27 in which the array is one-dimensional.

29. The plurality of claim 27 in which the array is two-dimensional.

30. The plurality of claim 27 in which the array is three-dimensional.

31. The plurality of claim 22 in which each template molecule is a peptide of from 3 to 7 amino acids in length.

32. The plurality of claim 22 which comprises imprint compositions defining imprints of the complete set of peptides of 7 amino acids in length.

* * * * *

UNITED STATES PATENT AND TRADEMARK OFFICE
CERTIFICATE OF CORRECTION

| | |
|---|---|
| PATENT NO. | : 6,979,573 B2 |
| APPLICATION NO. | : 09/895644 |
| DATED | : December 27, 2005 |
| INVENTOR(S) | : Chin-Shiou Huang |

Page 1 of 1

It is certified that error appears in the above-identified patent and that said Letters Patent is hereby corrected as shown below:

In Column 11, Line 44, Please delete [P-mercaptoethanol] and insert --β-mercaptoethanol--.

In Column 13, Line 13, Please delete [I] after "from" and insert --1--.

Signed and Sealed this

Twenty-eighth Day of November, 2006

JON W. DUDAS
*Director of the United States Patent and Trademark Office*